(12) United States Patent
Lee et al.

(10) Patent No.: US 11,905,539 B2
(45) Date of Patent: *Feb. 20, 2024

(54) ISOPROPYLMALATE SYNTHASE VARIANT AND A METHOD OF PRODUCING L-LEUCINE USING THE SAME

(71) Applicant: CJ Cheiljedang Corporation, Seoul (KR)

(72) Inventors: Ji Hye Lee, Gyeonggi-do (KR); Byeong Cheol Song, Gyeonggi-do (KR); Ae Ji Jeon, Seoul (KR); Jong Hyun Kim, Gyeonggi-do (KR); Hye Won Kim, Gyeonggi-do (KR)

(73) Assignee: CJ Cheiljedang Corporation, Seoul (KR)

(*) Notice: Subject to any disclaimer, the term of this patent is extended or adjusted under 35 U.S.C. 154(b) by 415 days.

This patent is subject to a terminal disclaimer.

(21) Appl. No.: 17/156,998

(22) Filed: Jan. 25, 2021

(65) Prior Publication Data

US 2021/0254111 A1 Aug. 19, 2021

Related U.S. Application Data

(63) Continuation of application No. 16/473,941, filed as application No. PCT/KR2017/011622 on Oct. 20, 2017, now Pat. No. 11,104,924.

(30) Foreign Application Priority Data

Dec. 28, 2016 (KR) .......................... 10-2016-0181343

(51) Int. Cl.
| | |
|---|---|
| C12P 13/06 | (2006.01) |
| C12N 9/10 | (2006.01) |
| C12N 15/52 | (2006.01) |
| C12N 15/77 | (2006.01) |
| C12N 15/74 | (2006.01) |

(52) U.S. Cl.
CPC ............ *C12P 13/06* (2013.01); *C12N 9/1025* (2013.01); *C12N 15/52* (2013.01); *C12N 15/74* (2013.01); *C12N 15/77* (2013.01); *C12Y 203/03013* (2013.01)

(58) Field of Classification Search
CPC ..... C12N 15/77; C12N 15/74; C12Y 2/02013
See application file for complete search history.

(56) References Cited

U.S. PATENT DOCUMENTS

| 6,403,342 B1 | 6/2002 | Gusyatiner et al. | |
|---|---|---|---|
| 10,351,859 B2* | 7/2019 | Song ...................... | C12N 15/77 |
| 2008/0138859 A1* | 6/2008 | Park ...................... | C07K 14/34 |
| | | | 435/252.32 |
| 2015/0079641 A1 | 3/2015 | Gerstmeir et al. | |

FOREIGN PATENT DOCUMENTS

| CN | 104480058 A | | 4/2015 |
|---|---|---|---|
| KR | 10-0220018 B1 | | 10/1999 |
| KR | 10-0438146 B1 | | 11/2004 |
| KR | 10-0620092 B1 | | 9/2006 |
| KR | 10-2011-0017747 A | | 2/2011 |
| KR | 10-2015-0003752 A | | 1/2015 |
| TW | 201502272 A | * | 1/2015 |

OTHER PUBLICATIONS

NCBI, GenBank accession No. ALP49010.1, Dec. 22, 2015.
NCBI, GenBank accession No. CP012194.1, Dec. 22, 2015.
Gui et al., "Complete genome sequence of *Corynebacterium glutamicum* CP, a Chinese L-leucine producing strain",Journal of Biotechnology, vol. 220, p. 64-65, 2016.
Vogt et al. "Pushing product formation to its limit: Metabolic engineering of *Corynebacterium glutamicum* for L-leucine overproduction." Metabolic Engineering, vol. 22 pp. 40-52 (2014).
Notice of Allowance issued in Korean Patent Application No. 10-2017-0136244 dated Dec. 3, 2019.
Office Action in related U.S. Appl. No. 16/473,941 dated Oct. 23, 2020.
Extended Search Report issued in European Patent Application No. 17889165.1, dated Jul. 7, 2020.
Wang et al., Metabolic engineering of L=leucine production in *Escherichia coli* and Corynebacterium glutamicum: a review. Critical Reviews in Biotechnology, 39(5): 633-647, 2019.
Yindeeyoungyeon et al., Characterization of alpha-isopropylmalate synthases containing different copy numbers of tandem repeats in *Mycobacterium tuberculosis*: BMC Microbiology 9:122, pp. 1-10, 2009.

\* cited by examiner

*Primary Examiner* — Allison M Fox
*Assistant Examiner* — Qing Xu
(74) *Attorney, Agent, or Firm* — Knobbe, Martens, Olson & Bear, LLP

(57) ABSTRACT

A novel modified polypeptide having an isopropylmalate synthase activity, a polynucleotide encoding the same, a microorganism including the polypeptide, and a method of producing L-leucine by culturing the microorganism.

10 Claims, No Drawings

Specification includes a Sequence Listing.

US 11,905,539 B2

ISOPROPYLMALATE SYNTHASE VARIANT AND A METHOD OF PRODUCING L-LEUCINE USING THE SAME

CROSS-REFERENCE TO RELATED APPLICATIONS

This application is a continuation of U.S. application Ser. No. 16/473,941, filed Jun. 26, 2019, which is the U.S. National Phase under 35 U.S.C. § 371 of International Patent Application No. PCT/KR2017/011622, filed Oct. 20, 2017, which was published in Korean as WO 2018/124440 on Jul. 5, 2018, which claims priority to Korean Patent Application No. filed Dec. 28, 2016, the entire contents of which are incorporated herein by reference.

SEQUENCE LISTING STATEMENT

The present application contains a Sequence Listing, which is being submitted via EFS-Web on even date herewith. The Sequence Listing is submitted in a file entitled "Sequence_Listing.txt," which was created on Sep. 26, 2019, and is approximately 121 kb in size. This Sequence Listing is hereby incorporated by reference.

TECHNICAL FIELD

The present disclosure relates to a novel modified polypeptide having an isopropylmalate synthase activity, a polynucleotide encoding the same, a microorganism comprising the polypeptide, and a method of producing L-leucine by culturing the microorganism.

BACKGROUND ART

L-Leucine is an essential amino acid, one which is expensive and widely used in medicaments, foods, feed additives, industrial chemicals, etc. In addition, L-leucine is mainly produced using a microorganism. Fermentation of branched-chain amino acids including L-leucine is mainly carried out through a microorganism of the genus *Escherichia* or a microorganism of the genus *Corynebacterium*, known to biosynthesize 2-ketoisocaproate as a precursor from pyruvic acid though several steps (Korean Patent Nos. 10-0220018 and 10-0438146).

Isopropyl malate synthase (hereinafter referred to as "IPMS"), which is an enzyme involved in the biosynthesis of leucine, is an enzyme of the first step in the biosynthesis of leucine, which converts 2-ketoisovalerate, produced during the valine biosynthetic pathway, to isopropylmalate, allowing the biosynthesis of leucine instead of valine, and thereby IPMS is an important enzyme in the process of leucine biosynthesis. However, the IPMS is subject to feedback inhibition by L-leucine, which is a final product, or derivatives thereof. Accordingly, although there is a variety of prior art relevant to IPMS variants which release feedback inhibition for the purpose of producing a high concentration of leucine (U.S. Patent Publication Application No. 2015-0079641 and U.S. Pat. No. 6,403,342), research is still continuing to discover better variants.

Technical Problem

The present inventors have endeavored to develop an IPMS variant that can be used for the production of L-leucine with a high concentration, and as a result, the present inventors developed a novel IPMS variant. It was confirmed that the variant released feedback inhibition by L-leucine, which is a final product, and enhanced an activity thereof such that the variant is capable of producing L-leucine at a high yield from a microorganism containing the same, thereby completing the present disclosure.

Technical Solution

An object of the present disclosure is to provide a novel modified polypeptide having an isopropylmalate, synthase activity.

Another object of the present disclosure is to provide a polynucleotide encoding the modified polypeptide.

Still another object of the present disclosure is to provide a microorganism of the genus *Corynebacterium* producing L-leucine, containing the polypeptide.

Still another object of the present disclosure is to provide a method of producing L-leucine by culturing the microorganism in a medium.

Advantageous Effects

The novel modified polypeptide having an activity of isopropylmalate synthase is a polypeptide in which the activity is increased compared to that of the wild-type and feedback inhibition by L-leucine is released, and thereby L-leucine can be produced in a high yield using such modified polypeptide.

BEST MODE FOR CARRYING OUT THE INVENTION

To achieve the above objects, an aspect of the present disclosure provides a novel modified polypeptide having an isopropylmalate synthase activity. The novel modified polypeptide may be a modified polypeptide having an isopropylmalate synthase activity, wherein arginine at position 558 from a N-terminus of a polypeptide consisting of the amino acid sequence of SEQ ID NO: 1 is substituted with an amino acid residue other than arginine, or glycine at position 561 from a N-terminus of a polypeptide consisting of the amino acid sequence of SEQ ID NO: 1 is substituted with an amino acid residue other than glycine. The modified polypeptide of the present disclosure not only has an activity higher than that of a polypeptide of SEQ ID NO: 1 having an isopropylmalate synthase activity, but also has a feature that feedback inhibition by L-leucine is released.

As used herein, the term "isopropylmalate synthase" refers to an enzyme converting 2-ketoisovalerate to isopropylmalate, which is a precursor of L-leucine, by reacting with acetyl-CoA. The isopropylmalate synthase of the present disclosure may be included as long as the enzyme has the conversion activity, regardless of an origin of a microorganism. Specifically, the isopropylmalate synthase may be an enzyme derived from a microorganism of the genus *Corynebacterium*. More specifically, the isopropylmalate synthase may be an isopropylmalate, synthase derived from *Corynebacterium glutamicum*, and specifically, it may include the amino acid sequence of SEQ ID NO: 1, but is not limited thereto. Additionally, the isopropylmalate synthase may include a polypeptide having homology of at least 80%, 90%, 95%, 96%, 97%, 98%, or 99% with the amino acid sequence of SEQ ID NO: 1. For example, it is obvious that an amino acid sequence having such homology and exhibiting an effect corresponding to that of the isopropylmalate synthase can be included within the scope of the present disclosure even if it has an amino acid sequence in which some of the sequences are deleted, modified, substituted, or added.

As used herein, the term "increase in activity of isopropylmalate synthase" refers to an increase in the conversion activity to isopropylmalate. Therefore, the modified polypeptide of the present disclosure has a higher level of the isopropylmalate conversion activity compared to a polypeptide of SEQ ID NO: 1 having the activity of isopropylmalate, synthase. The isopropylmalate conversion activity can be directly confirmed by measuring the level of isopropylmalate produced, or can be indirectly confirmed by measuring the level of CoA produced. As used herein, the term "increase in activity" may be used in combination with "enhanced activity". Further, isopropylmalate is a precursor of L-leucine, and thus the use of the modified polypeptide of the present disclosure results in producing a higher level of L-leucine compared to a polypeptide of SEQ ID NO: 1 having the activity of isopropylmalate synthase.

Additionally, unlike a polypeptide of SEQ ID NO: 1 having the activity of isopropylmalate synthase, the modified polypeptide of the present disclosure may be characterized in that feedback inhibition by L-leucine, which is a final product, or a derivative, thereof is released. As used herein, the term "feedback inhibition" refers to the inhibition of a reaction at the early state of an enzyme system by a final product in the enzyme system. For the objects of the present disclosure, the feedback inhibition may be feedback inhibition in which L-leucine or a derivative thereof inhibits the activity of isopropylmalate synthase, which mediates the first step of the biosynthetic pathway, but is not limited thereto. Therefore, when the feedback inhibition of isopropylmalate synthase is released, the productivity of L-leucine can be increased compared with the case of not releasing the same.

As used herein, the term "modification", "modified", or "variant" refers to a culture or an individual that shows an inheritable or non-heritable alternation in one stabilized phenotype. Specifically, the term "variant" may be intended to mean a variant in which its activity is efficiently increased because the amino acid sequence corresponding to Corynebacterium glutamicum-derived isopropylmalate synthase is modified compared to the wild-type, a variant in which feedback inhibition by L-leucine or a derivative thereof is released, or a variant in which the increase in activity and feedback inhibition are both released.

Specifically, the modified polypeptide of the present disclosure, which has the activity of isopropylmalate synthase, may be a modified polypeptide having an activity of isopropylmalate synthase, wherein arginine, an amino acid at position 558 from a N-terminus of a polypeptide consisting of the amino acid sequence of SEQ ID NO: 1, is substituted with an amino acid residue other than arginine, or glycine, an amino acid residue at position 561 from a N-terminus of a polypeptide consisting of the amino acid sequence of SEQ ID NO: 1, is substituted with an amino acid residue other than glycine. The amino acid other than arginine may include alanine, leucine, isoleucine, valine, proline, phenylalanine, tryptophan, methionine, glycine, serine, threonine, cysteine, tyrosine, asparagine, glutamine, lysine, histidine, aspartic acid, and glutamic acid; and the amino acid other than glycine may include alanine, leucine, isoleucine, valine, proline, phenylalanine, tryptophan, methionine, arginine, serine, threonine, cysteine, tyrosine, asparagine, glutamine, lysine, histidine, aspartic acid, and glutamic acid; but the amino acids are not limited thereto. More specifically, the modified polypeptide may be a modified polypeptide, wherein arginine, an amino acid residue at position 558 from a N-terminus of a polypeptide consisting of the amino acid sequence of SEQ ID NO: 1, is substituted with histidine, alanine, or glutamine; or glycine, an amino acid residue at position 561 from a N-terminus of a polypeptide consisting of the amino acid sequence of SEQ ID NO: 1, is substituted with aspartic acid, arginine, or tyrosine, but is not limited thereto. Additionally, the modified polypeptide may be one in which the arginine at position 558 is substituted with histidine, alanine, or glutamine; and the glycine at position 561 is substituted with aspartic acid, arginine, or tyrosine, but is not limited thereto. Most specifically, the modified polypeptide may include an amino acid sequence of any one of SEQ ID NO: 21 to SEQ ID NO: 35.

Additionally, the modified polypeptide may include a polypeptide having homology of at least 80%, 90%, 95%, 96%, 97%, 98%, or 99% with the amino acid sequence of any one of SEQ ID NO: 21 to SEQ ID NO: 35. For example, it is obvious that an enzyme variant having an amino acid sequence, in which some of the sequences are deleted, modified, substituted, or added while the modified amino acid sequence corresponding to the amino acid sequence at positions 558 and/or 561 is fixed, should also belong to the scope of the present disclosure as long as the amino acid sequence has the homology above and exhibits an effect corresponding to that of isopropylmalate synthase. On the other hand, positions 558 and 561, which are specific modification positions, refer to positions that are determined based on the N-terminus in the amino acid sequence of SEQ ID NO: 1, and therefore, the fact that such positions are determined by considering the number of the amino acids which are added to or deleted from the N-terminus of SEQ ID NO: 1 is obvious to one of ordinary skill in the art, and thereby also belongs to the scope of the present disclosure. For example, leuA, which is the gene encoding isopropylmalate synthase, was represented by SEQ ID NO: 1 consisting of 616 amino acids. However, in some references, the translation initiation codon is indicated 35 amino acids downstream of the sequence of the leuA gene, i.e., a gene consisting of 581 amino acids. In such a case, the $558^{th}$ amino acid is interpreted as the $523^{rd}$ amino acid and the $561^{st}$ amino acid as the $526^{th}$ amino acid, and is thereby included in the scope of the present disclosure.

As used herein, the term "homology" refers to a percentage of identity between two polynucleotides or polypeptide moieties. The homology between sequences from a moiety to another moiety may be determined by the technology known in the art. For example, the homology may be determined by directly arranging the sequence information, i.e., parameters such as score, identity, similarity, etc., of two polynucleotide molecules or two polypeptide molecules using an easily accessible computer program (Example: BLAST 2.0). Additionally, the homology between polynucleotides may be determined by hybridizing polynucleotides under the condition of forming a stable double-strand between the homologous regions, disassembling with a single strand-specific nuclease, followed by size determination of the disassembled fragments.

Another aspect of the present disclosure provides a polynucleotide encoding the modified polypeptide.

The polynucleotide may be a polynucleotide encoding a modified polypeptide having the activity of isopropylmalate synthase, wherein arginine, an amino acid at position 558 from a N-terminus of a polypeptide consisting of the amino acid sequence of SEQ ID NO: 1, is substituted with another amino acid residue other than arginine, or glycine, an amino acid residue at position 561 from a N-terminus of a polypeptide consisting of the amino acid sequence of SEQ ID NO: 1, is substituted with another amino acid residue other than glycine. Specifically, a polynucleotide encoding a polypeptide including the amino acid sequence of SEQ ID NOs: 21 to 35 and having an activity of isopropylmalate synthase; a modified polypeptide having homology of at least 80%, 90%, 95%, 96%, 97%, 98%, or 99% with the polypeptide above; or encoding a modified polypeptide having an activity of isopropylmalate synthase, in which some of the sequences are deleted, modified, substituted, or added while the modified amino acid sequence at positions 558 and/or 561, which are specific modification positions in the polypeptide above, is fixed may be included without limitation. Alternately, the probe that can be prepared from a known gene sequence, for example, a sequence encoding a protein having activity of Isopropylmalate synthase by hybridization of a complementary sequence for all or part of the nucleotide sequence above under stringent conditions, can be included without limitation.

As used herein, the term "stringent conditions" refers to conditions under which a so-called hybrid is formed while non-specific hybrids are not formed. Examples of such conditions include conditions under which genes having high degrees of homology, such as genes having a homology of 80% or more, specifically 90% or more, more specifically 95% or more, furthermore specifically 97% or more, and most specifically 99% or more, hybridize with each other while genes having low degrees of a homology do not hybridize with each other, or conditions under which genes are washed 1 time, and specifically 2 and 3 times, at a temperature and a salt concentration equivalent to 60° C., 1×SSC, and 0.1% SDS, specifically 60° C., 0.1×SSC, and 0.1% SDS, and more specifically 68° C., 0.1×SSC, and 0.1% SDS, which are the conditions for washing of ordinary Southern hybridization (Sambrook et al., Molecular Cloning: A Laboratory Manual, 3rd Ed., Cold Spring Harbor Laboratory Press, Cold Spring Harbor, N.Y. (2001)).

The probe used in the hybridization may be a part of the complementary sequence of the nucleotide sequence. Such probe can be constructed by PCR using an oligonucleotide prepared based on a known sequence as a primer and a gene fragment containing such nucleotide sequence as a template. For example, a gene fragment having a length of about 300 bp can be used as a probe. More specifically, in the case of using a probe having a length (about 300 bp), 50° C., 2×SSC, and 0.1% SDS may be suggested for the washing conditions of hybridization.

On the other hand, the polynucleotide may be a polynucleotide having a nucleotide sequence of any one of SEQ ID NO: 36 to SEQ ID NO: 50, and it is obvious that the polynucleotide also includes a polynucleotide that can be translated into the modified polypeptide by codon degeneracy.

Still another aspect of the present disclosure is to provide a microorganism of the genus *Corynebacterium* producing L-leucine, containing the modified polypeptide.

In the present disclosure, the microorganism may include all of a microorganism artificially produced through transformation or a naturally-occurring microorganism.

As used herein, the term "transformation" refers to the introduction of a gene into a host cell for expression. In the present disclosure, the transformation method includes any method that introduces a gene into a cell and can be carried out by selecting a suitable standard technique known in the art. Examples of the transformation method are electroporation, calcium phosphate co-precipitation, retroviral infection, microinjection, DEAE-dextran, cationic liposome, heat shock method, etc., but are not limited thereto.

The gene to be transformed may include both a form inserted into the chromosome of a host cell and a form located outside the chromosome, as long as it can be expressed in the host cell. In addition, the gene includes DNA and RNA as a polynucleotide capable of encoding a polypeptide, and any gene that can be introduced and expressed in the host cell can be used without limitation. For example, the gene can be introduced into a host cell in a form of an expression cassette, which is a polynucleotide construct containing all elements required for self-expression. The expression cassette usually includes a promoter operably linked to the gene, a transcription termination signal, ribosome binding sites, and a translation termination signal. The expression cassette may be in a form of a self-replicable expression vector. In addition, the gene may be one introduced into a host cell itself or in a form of a polynucleotide construct, i.e., a form of a vector, and operably linked to the sequences required for expression in the host cell.

As used herein, the term "vector" refers to any carrier for cloning and/or transferring nucleotides to a host cell. A vector may be a replicon to allow for the replication of fragments combined with other DNA fragments. "Replicon" refers to any genetic unit acting as a self-replicating until for DNA replication in vivo, that is, replicable by self-regulation (e.g., plasmid, phage, cosmid, chromosome, and virus). The term "vector" may include viral and non-viral carriers for introducing nucleotides into a host cell in vitro, ex vivo, or in vivo, and may also include a mini-spherical DNA. For example, the vector may be a plasmid without a bacterial DNA sequence. Removal of bacterial DNA sequences which are rich in CpG area has been conducted to reduce silencing of the transgene expression and to promote more continuous expression from a plasmid DNA vector (for example, Ehrhardt, A. et al. (2003) Hum Gene Ther 10: 215-25; Yet, N. S. (2002) MoI Ther 5: 731-38; Chen, Z. Y. et al. (2004) Gene Ther 11: 856-64). The term "vector" also may include a transposon such as Sleeping Beauty (Izsvak et al. J. Mol. Biol. 302:93-102 (2000)), or an artificial chromosome. Examples of the vector typically used may be natural or recombinant plasmid, cosmid, virus, and bacteriophage. For example, as the phage vector or the cosmid vector, pWE15, M13, λMBL3, λMBL4, λIIXII, λASHII, λAPII, λt10, λt11, Charon4A, Charon21A, etc. may be used. In addition, as the plasmid vector, pDZ type, pBR type, pUC type, pBluescriptII type, pGEM type, pTZ type, pCL type, pET type, etc. may be used. Specifically, pECCG117 vector may be used. The vector that can be used in the present disclosure is not particularly limited, and the known expression/substitution vector may be used.

In addition, the vector may be a recombinant vector which may further include various antibiotic resistance genes.

As used herein, the term "antibiotic resistance gene" refers to a gene having resistance to antibiotics, and the cells comprising this gene survive even in the environment treated with the corresponding antibiotic. Therefore, the antibiotic resistance gene can be effectively used as a selection marker for a large-scale production of plasmids in microorganisms, such as *E. coli*, etc. In the present invention, as the antibiotic resistance gene is not a factor that significantly affects the expression efficiency which is obtained by an optimal combination of components of the vector which is the key feature of the present invention, any common antibiotic resistance gene can be used as a selection marker without limitation. Specifically, the resistance genes against ampicilin, tetracyclin, kanamycin, chloramphenicol, streptomycin, or neomycin can be used.

As used herein, the term "operably linked" refers to the operable linking of a regulatory sequence for nucleotide expression with a nucleotide sequence encoding a target protein for performing its general function, thereby affecting the expression of a coding nucleotide sequence. Operable linking with a vector can be made using a gene recombination technique known in the art, and site-specific DNA cleavage and ligation can be performed using a restriction enzyme and ligase known in the art.

As used herein, the term "host cell in which a vector is introduced (transformed)" refers to a cell transformed with a vector having a gene encoding one or more target proteins. The host cell may include any of a prokaryotic microorganism and a eukaryotic microorganism as long as the microorganism includes a modified polypeptide capable of producing isopropylmalate synthase by introducing the vector above. For example, the microorganism strain belonging to the genera of *Escherichia*, *Erwinia*, *Serratia*, *Providencia*, *Corynebacterium*, and *Brevibacterium* may be included. An example of the microorganism of the genus *Corynebacterium* may be *Corynebacterium glutamicum*, but is not limited thereto.

The microorganism of the genus *Corynebacterium* producing L-leucine, which is capable of expressing the modified polypeptide having the activity of isopropylmalate synthase, includes all microorganisms capable of expressing the modified polypeptide by various known methods in addition to the introduction of a vector.

Still another aspect of the present disclosure provides a method of producing L-leucine, comprising: (a) culturing the microorganism of the genus *Corynebacterium* producing L-leucine; and (b) recovering L-leucine from the cultured microorganism or the cultured medium.

As used herein, the term "culture" refers to culturing of the microorganism under appropriately controlled environmental conditions. The culturing process of the present disclosure may be carried out depending on a suitable medium and culture condition known in the art. Such culturing process can be easily adjusted and used by one of ordinary skill in the art depending on the strain to be selected. Specifically, the culture may be a batch type, a continuous type, and a fed-batch type, but is not limited thereto.

The carbon sources contained in the medium may include sugars and carbohydrates, such as glucose, sucrose, lactose, fructose, maltose, starch, and cellulose; oils and fats, such as soybean oil, sunflower oil, castor oil, coconut oil, etc.; fatty acids, such as palmitic acid, stearic acid, and linoleic acid; alcohols, such as glycerol and ethanol; and organic acids such as acetic acid. These materials may be used alone or in combinations thereof, but are not limited thereto. The nitrogen sources contained in the medium may include organic nitrogen sources, such as peptone, yeast extract, gravy, malt extract, corn steep liquor, and soybean; and inorganic nitrogen sources, such as urea, ammonium sulfate, ammonium chloride, ammonium phosphate, ammonium carbonate, and ammonium nitrate. These nitrogen sources may be used alone or in combinations thereof, but are not limited thereto. The phosphorous sources contained in the medium may include potassium dihydrogen phosphate, dipotassium hydrogen phosphate, and corresponding sodium-containing salts, but are not limited thereto. Additionally, metal salts such as magnesium sulfate or iron sulfate may be contained. In addition, amino acids, vitamins, suitable precursors, etc. may be contained. These media or precursors may be added in a batch culture process or a continuous culture process to a culture, but are not limited thereto.

pH of the culture may be adjusted during the cultivation by adding an appropriate compound such as ammonium hydroxide, potassium hydroxide, ammonia, phosphoric acid, and sulfuric acid, and the generation of foams may be inhibited during the cultivation by using an antifoaming agent such as fatty acid polyglycol ester. In order to maintain aerobic conditions of the culture, oxygen or oxygen-containing gas may be injected into the culture. In order to maintain anaerobic and microaerobic conditions, no gas may be injected or nitrogen, hydrogen, or carbon dioxide may be injected. The temperature of the culture may be 27° C. to 37° C., and specifically 30° C. to 35° C., but is not limited thereto. The period of cultivation may be continued as long as the desired amount of useful material is recovered, and preferably for 10 to 100 hours, but the period of cultivation is not limited thereto.

The step of recovering L-leucine produced in the culture step of the present disclosure can collect the desired L-leucine from the microorganism or the medium using a suitable method known in the art depending on culture methods. For example, centrifugation, filtration, anion exchange chromatography, crystallization, HPLC, etc. may be used, and a suitable method known in the art may be used to recover the desired L-leucine from the medium or the microorganism. Additionally, the recovery step above may include a purification process.

MODE FOR CARRYING OUT THE INVENTION

Hereinbelow, the present disclosure will be described in detail with accompanying exemplary embodiments. However, the exemplary embodiments disclosed herein are only for illustrative purposes and should not be construed as limiting the scope of the present disclosure.

Example 1: Confirmation of leuA Nucleotide Sequence of KCCM11661P, Microorganism Producing Leucine

*Corynebacterium glutamicum* ATCC14067 was inoculated into a seed medium having the ingredients described below at 121° C. for 15 minutes, cultured for 13 hours, and then 25 mL of the culture medium was recovered. The recovered culture medium was washed with a 100 mM citrate buffer and treated with N-methyl-N'-nitro-N-nitrosoguanidine (NTG) for 30 minutes to a final concentration of 400 µg/mL. Thereafter, the resultant was washed with a 100 mM phosphate buffer. The mortality rate of the strains treated with NTG was determined to be 99.6% as a result of smearing the strains on a minimal medium having the ingredients described below. In order to achieve variants resistant to norleucine (NL), the NTG-treated strains were smeared on the minimal media with final concentrations of 20 mM, 40 mM, and mM, cultured at 30° C. for 5 days, and then variants resistant to NL were obtained.

<Seed Medium>

Glucose (20 g), peptone (10 g), yeast extract (5 g), carbamide (1.5 g), $KH_2PO_4$ (4 g), $K_2HPO_4$ (8 g), $MgSO_4 \cdot 7H_2O$ (0.5 g), biotin (100 µg), thiamine hydrochloride (1,000 µg), calcium-pantothenic acid (2,000 µg), nicotinamide (2,000 µg; based on 1 liter of distilled water), pH 7.0

<Production Medium>

Glucose (100 g), $(NH_4)_2SO_4$ (40 g), soy protein (2.5 g), corn steep solid (5 g), urea (3 g), $KH_2PO_4$ (1 g), MgSO$_4$·7H$_2$O (0.5 g), biotin (100 µg), thiamine hydrochloride (1,000 µg), calcium-pantothenic acid (2000 µg), nicotinamide (3,000 µg), CaCO$_3$ (30 g; based on 1 liter of distilled water), pH 7.0

The variants obtained by the method above were designated as *Corynebacterium glutamicum* KCJ-24 and *Corynebacterium glutamicum* KCJ-28 and deposited to the Korean Culture Center of Microorganisms, an international depositary authority, on Jan. 22, 2015, under the Budapest Treaty, and as a result, *Corynebacterium glutamicum* KCJ-24 and *Corynebacterium glutamicum* KCJ-28 were deposited under Accession Nos. KCCM11661P and KCCM11662P, respectively. *Corynebacterium glutamicum* KCJ-24 and *Corynebacterium glutamicum* KCJ-28 produced L-leucine at a concentration of 2.7 g/L and 3.1 g/L, respectively. Therefore, it was confirmed that the productivity of L-leucine produced from the variants was higher than that of the wild-type.

Additionally, an attempt was made to confirm whether the variation of leuA encoding isopropylmalate synthase (IPMS) occurred in the variant KCCM11661P. The amino acid sequence (SEQ ID NO: 1) of wild-type leuA was confirmed by referring to WP_003863358.1 of Genebank. The chromosomal DNA of the variant was amplified using a polymerase chain reaction (hereinafter referred to as 'PCR') method. Although it is known that the leuA gene consists of 616 amino acids, in some references, it is published that the translation initiation codon is indicated 35 amino acids downstream of the sequence of the leuA gene, and thereby the leuA gene consists of 581 amino acids. In such a case, the position number indicating the variation of the corresponding amino acid can vary. Therefore, in cases where the leuA gene is considered to consist of 581 amino acids, the variation position is additionally indicated in parenthesis.

Specifically, PCR was performed using the chromosomal DNA of the variant as a template and using primers of SEQ ID NOs: 3 and 4 under the following conditions: denaturation at 94° C. for 1 minute; annealing at 58° C. for 30 seconds; and polymerization at 72° C. for 2 minutes using Taq DNA polymerase. Such PCR was repeated a total of 28 times to amplify a fragment of about 2,700 base pairs. The nucleotide sequence of the fragment was analyzed using the same primer, and as a result, it was confirmed that G, which is the 1673$^{rd}$ nucleotide of leuA in KCCM11661P, was substituted with A. This result implies that arginine, which is the 558$^{th}$ (or 523'd; hereinafter only indicated as 558$^{th}$) amino acid, is substituted with histidine. In addition, it was also confirmed that GC, which are the 1682$^{nd}$ and 1683$^{rd}$ nucleotides, were substituted with AT. This result also implies that glycine, which is the 561$^{st}$ (or 526$^{th}$, hereinafter only indicated as 561$^{st}$) amino acid, is substituted with aspartic acid.

Example 2: Production of Substitution Vector of IPMS Variant

In order to produce a vector containing the modified nucleotide sequence confirmed in Example 1, PCR was performed using the chromosomal DNA of the variant above as a template and using primers of SEQ ID NOs: 5 and 6 under the following conditions: denaturation at 94° C. for 1 minute; annealing at 58° C. for 30 seconds; and polymerization at 72° C. for 1 minute using Pfu DNA polymerase. Such PCR was repeated a total of 25 times to amplify a fragment of about 1,460 base pairs with SalI and XbaI restriction enzyme sites. The amplified fragment was treated with restriction enzymes, SalI and XbaI, and then pDZ-leuA (R558H, G561D) was prepared by ligation with the vector pDZ (Korean Patent No: 10-0924065 and International Patent Publication No. 2008-033001) treated with the same enzymes. Additionally, in order to prepare a vector with each variation, ATCC14067 was used as a template, and then 2 fragments were amplified using primers 5 and 7, and primers 8 and 6, respectively. PCR was performed using the two prepared fragments as templates under the following conditions: denaturation at 94° C. for 1 minute; annealing at 58° C. for 30 seconds; and polymerization at 72° C. for 1 minute using Pfu DNA polymerase. Such PCR was repeated a total of 25 times to amplify a fragment of about 1,460 base pairs with SalI and XbaI restriction enzyme sites. The amplified fragment was treated with restriction enzymes SalI and XbaI, and then pDZ-leuA (R558H) was prepared by ligation with pDZ treated with the same enzymes. pDZ-leuA (G561D) was prepared using primers 5 and 9, and primers 10 and 6 by the same method above.

Example 3: Production of Substitution Strain of IPMS Variant

*Corynebacterium glutamicum* ATCC14067 was used as a parent strain in order to prepare a strain containing the leuA-modified nucleotide sequence which was found in the modified strain above.

*Corynebacterium glutamicum* ATCC14067 was transformed with the vectors pDZ-leuA (R558H), pDZ-leuA (G561D), and pDZ-leuA (R558H, G561D), which were prepared in Example 2 by electroporation. Each of the strains prepared through the secondary crossover was designated as 14067::leuA (R558H), 14067::leuA (G561D), and 14067::leuA (R558H, G561D). In order to confirm whether the nucleotide of leuA was substituted, PCR was performed using primers of SEQ ID NOs: 3 and 4 under the following conditions: denaturation at 94° C. for 1 minute; annealing at 58° C. for 30 seconds; and polymerization at 72° C. for 2 minutes using Taq DNA polymerase. Such PCR was repeated a total of 28 times to amplify a fragment of about 2,700 base pairs. Thereafter, the substitution of the nucleotide of leuA was confirmed by analyzing the nucleotide sequence with the same primer.

The strain, 14067::leuA (R558H, G561D) which was transformed with the vector pDZ-leuA (R558H, G561D), was designated as KCJ-0148, and deposited to the Korean Culture Center of Microorganisms on Jan. 25, 2016, and as a result, the strain was deposited under Accession No. KCCM11811P.

Example 4: Production of L-Leucine in Substitution Strain of IPMS Variant

In order to produce L-leucine from *Corynebacterium glutamicum* 14067::leuA (R558H), 14067::leuA (G561D), and 14067::leuA (R558H, G561D), which were prepared in Example 3, cultivation was carried out in the following manner.

A platinum loop of each of the parent strain, *Corynebacterium glutamicum* ATCC14067, and the prepared *Corynebacterium glutamicum* 14067::leuA (R558H), 14067::leuA (G561D), and 14067::leuA (R558H, G561D) strains was inoculated into a corner-baffled flask (250 mL) containing a production medium (25 mL). Thereafter, L-leucine was produced by incubating in a shaking water bath at 30° C. at a rate of 200 rpm for 60 hours.

After completion of the incubation, the amount of L-leucine produced was measured by high performance liquid chromatography. The concentration of L-leucine in the culture medium for each experimental strain is shown in Table 1 below.

TABLE 1

Production of L-leucine in
substitution strain of IPMS variant

| Strain | L-Leucine concentration (g/L) |
|---|---|
| ATCC14067 | 0.1 |
| 14067::leuA (R558H) | 1.2 |
| 14067::leuA (G561D) | 1.6 |
| 14067::leuA (R558H, G561D) | 2.5 |

As shown in Table 1 above, it was confirmed that the L-leucine productivity of the L-leucine-producing strains, *Corynebacterium glutamicum* 14067::leuA (R558H), 14067::leuA (G561D), and 14067::leuA (R558H, G561D), which have the R558H, G561D, or R558H/G561D variation in the leuA gene, was enhanced about 12- to 25-fold compared to that of the parent strain, *Corynebacterium glutamicum* ATCC14067.

Example 5: Production of IPMS Variant-Overexpressing Vector

In order to produce an expression vector containing the modified nucleotide sequence confirmed in Example 1, PCR was carried out using ATCC14067 and the chromosomal DNA of the 3 variants prepared in Example 3 as templates and using primers of SEQ ID NOs: 11 and 12 under the following conditions: denaturation at 94° C. for 1 minute; annealing at 58° C. for 30 seconds; and polymerization at 72° C. for 1 minute using Pfu DNA polymerase. Such PCR was repeated a total of 25 times to amplify a fragment of about 2,050 base pairs with NdeI and XbaI restriction enzyme sites. The amplified fragment was treated with restriction enzymes, NdeI and XbaI, and then expression vectors p117_PCJ7-leuA (WT), p117_PCJ7-leuA (R558H), p117_PCJ7-leuA (G561D), and p117_ PCJ7-leuA (R558H, G561D) were prepared by ligation using p117_PCJ7 in which a PCJ7 promoter was inserted in the vector pECCG117 (Biotechnology letters Vol. 13, No. 10, p. 721-726 (1991)) treated with the same enzymes. The PCJ7 promoter is a promoter that enhances gene expression, and is publicly known in Korean Patent No. 10-0620092 and International Patent Publication No. 2006-065095.

Example 6: Production of Strain Transformed with IPMS Variant-Overexpressing Vector In order to produce a strain transformed with an overexpression vector containing the leuA modified nucleotide sequence prepared in Example 5, the parent strain, which is wild-type *Corynebacterium glutamicum* ATCC14067, and the leucine-producing strains KCCM11661P and KCCM11662P were used.

Each of the vectors p117_PCJ7-leuA (WT), p117_PCJ7-leuA (R558H), p117_PCJ7-leuA (G561D), and p117_PCJ7-leuA (R558H, G561D), prepared in Example 5, was transformed with *Corynebacterium glutamicum* ATCC14067, KCCM11661P, and KCCM11662P by electroporation. As a result, 14067::p117_PCJ7-leuA (WT), 14067::p117_PCJ7-leuA (R558H), 14067::p117_PCJ7-leuA (G561D), 14067:: p117_PCJ7-leuA (R558H,G561D); KCCM11661P:: p117_PCJ7-leuA (WT), KCCM11661P::p117_PCJ7-leuA (R558H), KCCM11661P::p117_PCJ7-leuA (G561D), KCCM11661P::p117_PCJ7-leuA (R558H, G561D); and KCCM11662P::p117_PCJ7-leuA (WT), KCCM11662P:: p117_PCJ7-leuA (R558H), KCCM11662P::p117_PCJ7-leuA (G561D), KCCM11662P::p117_PCJ7-leuA (R558H, G561D) were produced.

Example 7: Production of L-Leucine in Strain Transformed with IPMS Variant-Overexpressing Vector In order to produce L-leucine from the L-leucine-producing strains, *Corynebacterium glutamicum* 14067:: p117_PCJ7-leuA (WT), 14067::p117_PCJ7-leuA (R558H), 14067::p117_PCJ7-leuA (G561D), 14067::p117_PCJ7-leuA (R558H, G561D); KCCM11661P::p117_PCJ7-leuA (WT), KCCM11661P::117PCJ7-leuA (R558H), KCCM11661P::p117_PCJ7-leuA (G561D), KCCM11661P::p117_PCJ7-leuA (R558H, G561D); and KCCM11662P::p117_PCJ7-leuA (WT), KCCM11662P:: p117_PCJ7-leuA (R558H), KCCM11662P::p117_PCJ7-leuA (G561D), KCCM11662P::p117_PCJ7-leuA (R558H, G561D), which were produced in Example 6, cultivation was carried out in the following manner A platinum loop of each of the parent strains, *Corynebacterium glutamicum* ATCC14067, KCCM11661P, and KCCM11662P, and the strains produced in Example 6 was inoculated into a corner-baffled flask (250 mL) containing a production medium (25 mL). Thereafter, L-leucine was produced by incubating in a shaking water bath at 30° C. at a rate of 200 rpm for 60 hours.

After completion of the incubation, the amount of L-leucine produced was measured by high performance liquid chromatography. The concentration of L-leucine in the culture medium for each experimental strain is shown in Table 2 below.

TABLE 2

Production of L-leucine in
strain overexpressing IPMS variant

| Strain | L-Leucine concentration (g/L) |
|---|---|
| ATCC14067 | 0.1 |
| 14067::p117_PCJ7-leuA (WT) | 0.3 |
| 14067::p117_PCJ7-leuA (R558H) | 4.5 |
| 14067::p117_PCJ7-leuA (G561D) | 5.1 |
| 14067::p117_PCJ7-leuA (R558H, G561D) | 9.8 |
| KCCM11661P | 2.7 |
| KCCM11661P::p117_PCJ7-leuA (WT) | 3.0 |
| KCCM11661P::p117_PCJ7-leuA (R558H) | 6.1 |
| KCCM11661P::p117_PCJ7-leuA (G561D) | 6.8 |
| KCCM11661P::p117_PCJ7-leuA (R558H, G561D) | 12.3 |
| KCCM11662P | 3.1 |
| KCCM11662P::p117_PCJ7-leuA (WT) | 3.3 |
| KCCM11662P::p117_PJ7-leuA (R558H) | 6.3 |
| KCCM11662P::p117_PCJ7-leuA (G561D) | 6.9 |
| KCCM11662P::p117_PCJ7-leuA (R558H, G561D) | 13.1 |

As shown in Table 2 above, it was confirmed that the L-leucine production of the L-leucine-producing strains, 14067::p117_PCJ7-leuA (R558H), 14067::p117_PCJ7-leuA (G561D), and 14067::p117_PCJ7-leuA (R558H, G561D), which were transformed with the overexpression vector containing variation of the leuA gene in the strain ATCC14067, was enhanced 45- to 98-fold compared to that of the parent strain ATCC14067; the L-leucine production of the L-leucine-producing strains, KCCM11661P::p117_PCJ7-leuA (R558H), KCCM11661P::p117_PCJ7-leuA (G561D), and KCCM11661P::p117_PCJ7-leuA (R558H, G561D), which were transformed with the overexpression vector containing variation of the leuA gene in the strain KCCM11661P, was enhanced 2.3- to 4.5-fold compared to that of the parent strain KCCM11661P; and that the L-leucine production of the L-leucine-producing strains, KCCM11662P::p117_PCJ7-leuA (R558H), KCCM11662P::p117_PCJ7-leuA (G561D), and KCCM11662P::p117_PCJ7-leuA (R558H,G561D), which were transformed with the overexpression vector containing variation of the leuA gene in the strain KCKCM11662P, was enhanced 2- to 4.2-fold compared to that of the parent strain KCCM11662P.

Example 8: Measurement of Isopropylmalate Synthase Activity in Strain Transformed with leuA-Overexpressing Vector In order to measure an isopropylmalate synthase activity in the L-leucine-producing strains, Corynebacterium glutamicum 14067::p117_PCJ7-leuA (WT), 14067::p117_PCJ7-leuA (R558H), 14067::p117_PCJ7-leuA (G561D), and 14067::p117_PCJ7-leuA (R558H, G561D), produced in Example 6, experiments were carried out in the following manner A platinum loop of each of the 4 strains above was inoculated into a corner-baffled flask (250 mL) containing the seed medium (25 mL). Thereafter, the resultants were incubated in a shaking water bath at 30° C. at a rate of 200 rpm for 16 hours. After completion of the incubation, the culture medium was centrifuged to discard the supernatant, the pellet was washed and mixed with a lysis buffer, and the cells were pulverized with a bead homogenizer. The proteins present in the lysate were quantitated according to the Bradford assay, and the activity of isopropylmalate synthase was measured by measuring the CoA produced when the lysate containing proteins (100 µg/mL) was used. The measurement results of the isopropylmalate synthase activity in each strain are shown in Table 3 below.

TABLE 3

| Strain | Relative IPMS activity (%) |
|---|---|
| 14067::p117_PCJ7-leuA (WT) | 100 |
| 14067::p117_PCJ7-leuA (R558H) | 105 |
| 14067::p117_PCJ7-leuA (G561D) | 130 |
| 14067::p117_PCJ7-leuA (R558H, G561D) | 328 |

In order to confirm the degree of release of feedback inhibition by leucine in the enzyme, the isopropylmalate synthase activity was measured by measuring the CoA produced when the lysate containing proteins (100 µg/mL) was used under the condition where leucine (3 g/L) was added. The measurement results of the isopropylmalate synthase activity in each strain are shown in Table 4 below.

TABLE 4

| Strain | Leucine 0 g/L Relative IPMS activity (%) | Leucine 2 g/L |
|---|---|---|
| 14067::p117_PCJ7-leuA (WT) | 100 | 24 |
| 14067::p117_PCJ7-leuA (R558H) | 100 | 61 |

TABLE 4-continued

| Strain | Leucine 0 g/L Relative IPMS activity (%) | Leucine 2 g/L |
|---|---|---|
| 14067::p117_PCJ7-leuA (G561D) | 100 | 70 |
| 14067::p117_PCJ7-leuA (R558H, G561D) | 100 | 89 |

As shown in Tables 3 and 4 above, it was confirmed that the isopropylmalate synthase activity of the L-leucine-producing strains, Corynebacterium glutamicum 14067::p117_PCJ7-leuA (R558H), 14067::p117_PCJ7-leuA (G561D), and 14067::p117_PCJ7-leuA (R558H, G561D), which were transformed with the vector expressing the IPMS variant, were enhanced 1.05-fold, 1.3-fold, and 3.2-fold, respectively, compared to that of the control, Corynebacterium glutamicum 14067::p117_PCJ7-leuA (WT). In addition, the L-leucine-producing strains maintained their IPMS activity at 61%, 70%, and 89%, respectively, even when leucine (2 g/L) was added, confirming that feedback inhibition by leucine was released.

Example 9: Production of Vector for Improving Isopropylmalate Synthase (IPMS) Variant In Examples 4, 7, and 8, since it was confirmed that the $558^{th}$ and $561^{st}$ amino acids in the amino acid sequence (SEQ ID NO: 1) of isopropylmalate synthase were important sites for the activity of the IPMS variant enzyme, the attempt was made to confirm whether the enzyme activity was enhanced or whether feedback inhibition was further released when substituted with an amino acid other than the amino acids in the variant. Therefore, an attempt was made to prepare a variant substituted with an amino acid of other amino acid groups capable of causing structural variations.

A variant in which the $558^{th}$ amino acid, arginine, was substituted with alanine (Ala) or glutamine (Gln) was prepared. The vector p117_PCJ7-leuA (R558A), in which the $558^{th}$ amino acid is substituted with alanine (Ala), and the vector p117_PCJ7-leuA (R558Q), in which the $558^{th}$ amino acid is substituted with glutamine (Gln), were prepared using a site-directed mutagenesis method and by using the vector p117_PCJ7-leuA (R558H) as a template, the primer of SEQ ID NOs: 13 and 14, and the primer pair of SEQ ID NOs: 15 and 16.

A variant in which the $561^{st}$ amino acid, glycine, was substituted with arginine (Arg) or tyrosine (Tyr) was prepared. The vector p117_PCJ7-leuA (G561R), in which the $561^{st}$ amino acid is substituted with arginine (Arg), and the vector p117_PCJ7-leuA (G561Y), in which the $561^{st}$ amino acid is substituted with tyrosine (Tyr), were obtained using a site-directed mutagenesis method and by using p117_PCJ7-leuA (G561D) as a template, the primer of SEQ ID NOs: 17 and 18, and the primer pair of SEQ ID NOs: 19 and 20.

Example 10: Production of Strain in which Isopropylmalate-Modified Variant is Introduced In order to prepare a strain transformed with an expression vector containing the leuA-modified nucleotide sequence prepared in Example 9, wild-type Corynebacterium glutamicum ATCC14067 was used as a parent strain.

Each of the vectors, p117_PCJ7-leuA (R558A), p117_PCJ7-leuA (R558Q), p117_PCJ7-leuA (G561R), and p117_PCJ7-leuA (G561Y), which were prepared in Example 9, was transformed in Corynebacterium glutamicum ATCC14067 by electroporation to prepare 14067::

p117_PCJ7-leuA (R558A), 14067::p117_PCJ7-leuA (R558Q), 14067::p117_PCJ7-leuA (G561R), and 14067::p117_PCJ7-leuA (G561Y).

Example 11: Production of L-Leucine in Strain in which Isopropylmalate Synthase-Modified Variant is Introduced In order to produce L-leucine from the L-leucine-producing strains, *Corynebacterium glutamicum* 14067::p117_PCJ7-leuA (R558A), 14067::p117_PCJ7-leuA (R558Q), 14067::p117_PCJ7-leuA (G561R), and 14067::p117_PCJ7-leuA (G561Y), which were prepared in Example 10, cultivation was carried out in the following manner A platinum loop of each of the parent strain, *Corynebacterium glutamicum* ATCC14067, and the 4 strains above was inoculated into a corner-baffled flask (250 mL) containing a production medium (25 mL). Thereafter, L-leucine was produced by incubating in a shaking water bath at 30° C. at a rate of 200 rpm for 60 hours.

After completion of the incubation, the amount of L-leucine produced was measured by high performance liquid chromatography. The concentration of L-leucine in the culture medium for each experimental strain is shown in Table 5 below.

TABLE 5

Production of L-leucine in strain overexpressing IPMS variant

| Strain | L-Leucine concentration (g/L) |
|---|---|
| ATCC14067 | 0.1 |
| 14067::p117_PCJ7-leuA (WT) | 0.3 |
| 14067::p117_PCJ7-leuA (R558H) (Example 7) | 4.5 |
| 14067::p117_PCJ7-leuA (R558A) | 3.8 |
| 14067::p117_PCJ7-leuA (R558Q) | 3.2 |
| 14067::p117_PCJ7-leuA (G561D) (Example 7) | 5.1 |

TABLE 5-continued

Production of L-leucine in strain overexpressing IPMS variant

| Strain | L-Leucine concentration (g/L) |
|---|---|
| 14067::p117_PCJ7-leuA (G561R) | 4.0 |
| 14067::p117_PCJ7-leuA (G561Y) | 3.6 |

As shown in Table 5 above, it was confirmed that the L-leucine productivity of the L-leucine-producing strains, *Corynebacterium glutamicum* 14067::p117_PCJ7-leuA (R558A) and 14067::p117_PCJ7-leuA (R558Q), was improved 32- to 38-fold compared to the parent strain, *Corynebacterium glutamicum* ATCC14067.

Additionally, it was confirmed that the L-leucine productivity of the L-leucine-producing strains, *Corynebacterium glutamicum* 14067::p117_PCJ7-leuA (G561R) and 14067::p117_PCJ7-leuA (G561Y), was improved about 36- to 40-fold compared to that of the parent strain, *Corynebacterium glutamicum* ATCC14067.

Based on the results above, it was confirmed the $558^{th}$ and $561^{st}$ amino acids in the amino acid sequence (SEQ ID NO: 1) of isopropylmalate synthase were important sites for the activity of the IPMS variant enzyme, and that even when each of the $558^{th}$ and $561^{st}$ amino acids of the wild type IPMS protein was substituted with histidine and aspartic acid, respectively, the L-leucine productivity was remarkably increased in the strain having such modification.

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

What is claimed is:

1. A modified microorganism belonging to the genus of *Corynebacterium* for producing L-leucine, comprising a modified polypeptide having an isopropylmalate synthase activity,
wherein glycine at position 561 from a N-terminus of a polypeptide consisting of the amino acid sequence of SEQ ID NO: 1 is substituted with aspartic acid in the modified polypeptide, and
wherein the modified microorganism has a resistance to norleucine or L-leucine, and
wherein a native promoter of a polynucleotide encoding the modified polypeptide in the microorganism is substituted with a promoter which enhances an expression of the polynucleotide compared to the native promoter.

2. The modified microorganism of claim 1, wherein the promoter which enhances an expression of the polynucleotide compared to the native promoter is a PCJ7 promoter.

3. The modified microorganism of claim 1, wherein the modified microorganism belonging to the genus of *Corynebacterium* is derived from a *Corynebacterium glutamicum*.

4. A method of producing L-leucine, comprising:
(a) culturing a modified microorganism belonging to the genus of *Corynebacterium* for producing L-leucine, in a medium to produce L-leucine, wherein the microorganism comprises a polynucleotide encoding a modified polypeptide having an isopropylmalate synthase activity, wherein glycine at position 561 from a N-terminus of a polypeptide consisting of the amino acid sequence of SEQ ID NO: 1 is substituted with aspartic acid in the modified polypeptide, wherein the modified microorganism has a resistance to norleucine or L-leucine, and wherein a native promoter of a polynucleotide encoding the modified polypeptide in the microorganism is substituted with a promoter which enhances an expression of the polynucleotide compared to the native promoter; and (b) recovering L-leucine from the cultured microorganism or the cultured medium.

5. The method of claim 4, wherein the promoter which enhances an expression of the polynucleotide compared to the native promoter is a PCJ7 promoter.

6. The method of claim 4, wherein the modified microorganism belonging to the genus of *Corynebacterium* is derived from a *Corynebacterium glutamicum*.

7. The modified microorganism of claim 1, wherein said modified microorganism is transformed with a vector comprising:
   i) the polynucleotide encoding the modified polypeptide having an isopropylmalate synthase activity; and
   ii) the promoter that is operatively connected to the polynucleotide, wherein the promoter is a non-native promoter of the polynucleotide and the expression of the polynucleotide is driven by the promoter, not the native promoter; and wherein the promoter enhances the expression of the polynucleotide, compared to the native promoter, thereby enhancing the productivity of L-leucine.

8. The modified microorganism of claim 7, wherein the promoter that enhances productivity of L-leucine operatively linked to the polynucleotide is a PCJ7 promoter.

9. The method of claim 4, wherein the microorganism is transformed with a vector comprising:
   i) the polynucleotide encoding the modified polypeptide having an isopropylmalate synthase activity; and
   ii) the promoter that is operatively connected to the polynucleotide, wherein the promoter is a non-native promoter of the polynucleotide and the expression of the polynucleotide is driven by the promoter, not the native promoter; and wherein the promoter enhances the expression of the polynucleotide, compared to the native promoter, thereby enhancing the productivity of L-leucine.

10. The method of claim 9, wherein the promoter that enhances productivity of L-leucine linked to the polynucleotide is a PCJ7 promoter.

* * * * *

UNITED STATES PATENT AND TRADEMARK OFFICE
CERTIFICATE OF CORRECTION

| | |
|---|---|
| PATENT NO. | : 11,905,539 B2 |
| APPLICATION NO. | : 17/156998 |
| DATED | : February 20, 2024 |
| INVENTOR(S) | : Ji Hye Lee et al. |

It is certified that error appears in the above-identified patent and that said Letters Patent is hereby corrected as shown below:

In the Specification

Column 1, Line 14, after "No." insert -- 10-2016-0181343, --.

Column 1, Line 46, delete "Isopropyl malate" and insert -- Isopropylmalate --.

Column 2, Line 10 (approx.), delete "isopropylmalate," and insert -- isopropylmalate --.

Column 2, Line 58, delete "isopropylmalate," and insert -- isopropylmalate --.

Column 3, Line 9, delete "isopropylmalate," and insert -- isopropylmalate --.

Column 3, Line 24, delete "derivative," and insert -- derivative --.

Column 5, Line 17 (approx.), delete "Isopropylmalate" and insert -- isopropylmalate --.

Column 6, Line 45, delete "λIIXII," and insert -- λIXII, --.

Column 7, Line 1, delete "ampicilin, tetracyclin," and insert -- ampicillin, tetracycline, --.

Column 8, Line 56, after "and" insert -- 50 --.

Column 8, Line 64, delete "7.0" and insert -- 7.0. --.

Column 9, Line 4, delete "7.0" and insert -- 7.0. --.

Column 9, Line 17, before "higher" insert -- 10-fold --.

Column 9, Line 22, delete "Genebank." and insert -- Genbank. --.

Signed and Sealed this
Second Day of July, 2024

Katherine Kelly Vidal
*Director of the United States Patent and Trademark Office*

CERTIFICATE OF CORRECTION (continued)
U.S. Pat. No. 11,905,539 B2

Column 9, Line 44, delete "1673$^{nd}$" and insert -- 1673$^{rd}$ --.

Column 11, Line 41, delete "p117_ PCJ7-leuA" and insert -- p117_PCJ7-leuA --.

Column 12, Line 24 (approx.), delete "manner" and insert -- manner. --.

Column 13, Line 28, delete "manner" and insert -- manner. --.

Column 15, Line 16 (approx.), delete "manner" and insert -- manner. --.

SEQUENCE LISTING

```
<160> NUMBER OF SEQ ID NOS: 50

<210> SEQ ID NO 1
<211> LENGTH: 616
<212> TYPE: PRT
<213> ORGANISM: Artificial Sequence
<220> FEATURE:
<223> OTHER INFORMATION: leuA AA

<400> SEQUENCE: 1

Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
            20                  25                  30

Gly Ser Ser Met Pro Val Asn Arg Tyr Met Pro Phe Glu Val Glu Val
        35                  40                  45

Glu Asp Ile Ser Leu Pro Asp Arg Thr Trp Pro Asp Lys Lys Ile Thr
    50                  55                  60

Val Ala Pro Gln Trp Cys Ala Val Asp Leu Arg Asp Gly Asn Gln Ala
65                  70                  75                  80
```

```
Leu Ile Asp Pro Met Ser Pro Glu Arg Lys Arg Met Phe Glu Leu
             85                  90                  95
Leu Val Gln Met Gly Phe Lys Glu Ile Glu Val Gly Phe Pro Ser Ala
            100                 105                 110
Ser Gln Thr Asp Phe Asp Phe Val Arg Glu Ile Ile Glu Lys Asp Met
            115                 120                 125
Ile Pro Asp Asp Val Thr Ile Gln Val Leu Val Gln Ala Arg Glu His
            130                 135                 140
Leu Ile Arg Arg Thr Phe Glu Ala Cys Glu Gly Ala Lys Asn Val Ile
145                 150                 155                 160
Val His Phe Tyr Asn Ser Thr Ser Ile Leu Gln Arg Asn Val Val Phe
                165                 170                 175
Arg Met Asp Lys Val Gln Val Lys Lys Leu Ala Thr Asp Ala Ala Glu
            180                 185                 190
Leu Ile Lys Thr Val Ala Gln Asp Tyr Pro Asp Thr Asn Trp Arg Trp
            195                 200                 205
Gln Tyr Ser Pro Glu Ser Phe Thr Gly Thr Glu Val Glu Tyr Ala Lys
            210                 215                 220
Glu Val Val Asp Ala Val Val Glu Val Met Asp Pro Thr Pro Glu Asn
225                 230                 235                 240
Pro Met Ile Ile Asn Leu Pro Ser Thr Val Glu Met Ile Thr Pro Asn
                245                 250                 255
Val Tyr Ala Asp Ser Ile Glu Trp Met His Arg Asn Leu Asn Arg Arg
            260                 265                 270
Asp Ser Ile Ile Leu Ser Leu His Pro His Asn Asp Arg Gly Thr Gly
            275                 280                 285
Val Gly Ala Ala Glu Leu Gly Tyr Met Ala Gly Ala Asp Arg Ile Glu
            290                 295                 300
Gly Cys Leu Phe Gly Asn Gly Glu Arg Thr Gly Asn Val Cys Leu Val
305                 310                 315                 320
Thr Leu Ala Leu Asn Met Leu Thr Gln Gly Val Asp Pro Gln Leu Asp
                325                 330                 335
Phe Thr Asp Ile Arg Gln Ile Arg Ser Thr Val Glu Tyr Cys Asn Gln
            340                 345                 350
Leu Arg Val Pro Glu Arg His Pro Tyr Gly Gly Asp Leu Val Phe Thr
            355                 360                 365
Ala Phe Ser Gly Ser His Gln Asp Ala Val Asn Lys Gly Leu Asp Ala
            370                 375                 380
Met Ala Ala Lys Val Gln Pro Gly Ala Ser Ser Thr Glu Val Ser Trp
385                 390                 395                 400
Glu Gln Leu Arg Asp Thr Glu Trp Glu Val Pro Tyr Leu Pro Ile Asp
            405                 410                 415
Pro Lys Asp Val Gly Arg Asp Tyr Glu Ala Val Ile Arg Val Asn Ser
            420                 425                 430
Gln Ser Gly Lys Gly Gly Val Ala Tyr Ile Met Lys Thr Asp His Gly
            435                 440                 445
Leu Gln Ile Pro Arg Ser Met Gln Val Glu Phe Ser Thr Val Val Gln
            450                 455                 460
Asn Val Thr Asp Ala Glu Gly Gly Glu Val Asn Ser Lys Ala Met Trp
465                 470                 475                 480
Asp Ile Phe Ala Thr Glu Tyr Leu Glu Arg Thr Ala Pro Val Glu Gln
            485                 490                 495
Ile Ala Leu Arg Val Glu Asn Ala Gln Thr Glu Asn Glu Asp Ala Ser
```

```
            500             505             510
Ile Thr Ala Glu Leu Ile His Asn Gly Lys Asp Val Thr Val Asp Gly
            515             520             525

His Gly Asn Gly Pro Leu Ala Ala Tyr Ala Asn Ala Leu Glu Lys Leu
        530             535             540

Gly Ile Asp Val Glu Ile Gln Glu Tyr Asn Gln His Ala Arg Thr Ser
545             550             555             560

Gly Asp Asp Ala Glu Ala Ala Tyr Val Leu Ala Glu Val Asn Gly
                565             570             575

Arg Lys Val Trp Gly Val Gly Ile Ala Gly Ser Ile Thr Tyr Ala Ser
            580             585             590

Leu Lys Ala Val Thr Ser Ala Val Asn Arg Ala Leu Asp Val Asn His
        595             600             605

Glu Ala Val Leu Ala Gly Gly Val
    610             615

<210> SEQ ID NO 2
<211> LENGTH: 1851
<212> TYPE: DNA
<213> ORGANISM: Artificial Sequence
<220> FEATURE:
<223> OTHER INFORMATION: leuA NT

<400> SEQUENCE: 2
```

| | | | | | |
|---|---|---|---|---|---|
| atgtctccta | acgatgcatt | catctccgca | cctgccaaga | tcgaaacccc | agttgggcct | 60 |
| cgcaatgaag | ccagccagc | atggaataag | cagcgtggct | cctcaatgcc | agttaaccgc | 120 |
| tacatgcctt | tcgaggttga | ggtagaagat | atttctctgc | cggaccgcac | ttggccagat | 180 |
| aaaaaaatca | ccgttgcacc | tcagtggtgt | gctgttgacc | tgcgtgacgg | caaccaggct | 240 |
| ctgattgatc | cgatgtctcc | tgagcgtaag | cgccgcatgt | ttgagctgct | ggttcagatg | 300 |
| ggattcaagg | aaatcgaggt | cggtttccct | tcagcttccc | agactgattt | tgatttcgtt | 360 |
| cgtgagatca | tcgaaaagga | catgatccct | gacgatgtca | ccattcaggt | tctggttcag | 420 |
| gctcgtgagc | acctgattcg | ccgtactttt | gaagcttgcg | aaggcgcaaa | aaacgttatc | 480 |
| gtgcacttct | acaactcaac | ctccatcctg | cagcgcaacg | tggtgttccg | catggacaag | 540 |
| gtgcaggtga | agaagctggc | taccgatgcc | gctgaactga | tcaagaccgt | cgctcaggat | 600 |
| tacccagaca | ccaactggcg | ctggcagtac | tcccctgagt | ccttcaccgg | cactgaggtt | 660 |
| gagtacgcca | aggaagttgt | ggacgcagtt | gttgaggtca | tggatccaac | tcctgagaac | 720 |
| ccaatgatca | tcaacctgcc | ttccaccgtt | gagatgatca | cccctaacgt | ttacgcagac | 780 |
| tccattgaat | ggatgcaccg | caatctaaac | cgtcgtgatt | ccattatcct | gtccctgcac | 840 |
| ccgcacaatg | accgtggcac | cggcgttggc | gcagctgagc | tgggctacat | ggctggcgct | 900 |
| gaccgcatcg | aaggctgcct | gttcggcaac | ggcgagcgca | ccggcaacgt | ctgcctggtc | 960 |
| accctggcac | tgaacatgct | gacccagggc | gttgaccctc | agctggactt | caccgatata | 1020 |
| cgccagatcc | gcagcaccgt | tgaatactgc | aaccagctgc | gcgttcctga | gcgccaccca | 1080 |
| tacggcggcg | acctggtctt | caccgctttc | tccggttccc | accaggacgc | tgtgaacaag | 1140 |
| ggtctggacg | ccatggctgc | caaggttcag | ccaggtgcta | gctccactga | agtttcttgg | 1200 |
| gagcagctgc | gcgacaccga | atgggaggtt | ccttacctgc | ctatcgatcc | aaaggatgtc | 1260 |
| ggtcgcgact | acgaggctgt | tatccgcgtg | aactcccagt | ccggcaagggg | cggcgttgct | 1320 |
| tacatcatga | agaccgatca | cggtctgcag | atccctcgct | ccatgcaggt | tgagttctcc | 1380 |

```
accgttgtcc agaacgtcac cgacgctgag ggcggcgagg tcaactccaa ggcaatgtgg    1440
gatatcttcg ccaccgagta cctggagcgc accgcaccag ttgagcagat cgcgctgcgc    1500
gtcgagaacg ctcagaccga aaacgaggat gcatccatca ccgccgagct catccacaac    1560
ggcaaggacg tcaccgtcga tggccacggc aacggcccac tggctgctta cgccaacgcg    1620
ctggagaagc tgggcatcga cgttgagatc caggaataca accagcacgc ccgcacctcg    1680
ggcgacgatg cagaagcagc cgcctacgtg ctggctgagg tcaacggccg caaggtctgg    1740
ggcgtcggca tcgctggctc catcacctac gcttcgctga aggcagtgac ctccgccgta    1800
aaccgcgcgc tggacgtcaa ccacgaggca gtcctggctg cggcgtttta a             1851
```

```
<210> SEQ ID NO 3
<211> LENGTH: 21
<212> TYPE: DNA
<213> ORGANISM: Artificial Sequence
<220> FEATURE:
<223> OTHER INFORMATION: leuA sequencing-1

<400> SEQUENCE: 3
agaaggacaa agcactcatc c                                              21

<210> SEQ ID NO 4
<211> LENGTH: 20
<212> TYPE: DNA
<213> ORGANISM: Artificial Sequence
<220> FEATURE:
<223> OTHER INFORMATION: leuA sequencing-2

<400> SEQUENCE: 4
tcgccctagt attctggcgt                                                20

<210> SEQ ID NO 5
<211> LENGTH: 30
<212> TYPE: DNA
<213> ORGANISM: Artificial Sequence
<220> FEATURE:
<223> OTHER INFORMATION: leuA sub F

<400> SEQUENCE: 5
acgcgtcgac ttgaccctca gctggacttc                                     30

<210> SEQ ID NO 6
<211> LENGTH: 28
<212> TYPE: DNA
<213> ORGANISM: Artificial Sequence
<220> FEATURE:
<223> OTHER INFORMATION: leuA sub R

<400> SEQUENCE: 6
gctctagaaa ttccctgtcg gtgaagca                                       28

<210> SEQ ID NO 7
<211> LENGTH: 33
<212> TYPE: DNA
<213> ORGANISM: Artificial Sequence
<220> FEATURE:
<223> OTHER INFORMATION: leuA 588 mut P-2

<400> SEQUENCE: 7
atcgtcgccc gaggtgtggg cgtgctggtt gta                                 33

<210> SEQ ID NO 8
<211> LENGTH: 33
```

<212> TYPE: DNA
<213> ORGANISM: Artificial Sequence
<220> FEATURE:
<223> OTHER INFORMATION: leuA 588 mut P-3

<400> SEQUENCE: 8
tacaaccagc acgcccacac ctcgggcgac gat                               33

<210> SEQ ID NO 9
<211> LENGTH: 35
<212> TYPE: DNA
<213> ORGANISM: Artificial Sequence
<220> FEATURE:
<223> OTHER INFORMATION: leuA 561 mut P-2

<400> SEQUENCE: 9
tgcttctgca tcgtcatccg aggtgcgggc gtgct                             35

<210> SEQ ID NO 10
<211> LENGTH: 32
<212> TYPE: DNA
<213> ORGANISM: Artificial Sequence
<220> FEATURE:
<223> OTHER INFORMATION: leuA 561 mut P-3

<400> SEQUENCE: 10
acgcccgcac ctcggatgac gatgcagaag ca                                32

<210> SEQ ID NO 11
<211> LENGTH: 33
<212> TYPE: DNA
<213> ORGANISM: Artificial Sequence
<220> FEATURE:
<223> OTHER INFORMATION: leuA over F

<400> SEQUENCE: 11
ggaattttcc atatgtctcc taacgatgca ttc                               33

<210> SEQ ID NO 12
<211> LENGTH: 28
<212> TYPE: DNA
<213> ORGANISM: Artificial Sequence
<220> FEATURE:
<223> OTHER INFORMATION: leuA over R

<400> SEQUENCE: 12
gctctagatc gccctagtat tctggcgt                                     28

<210> SEQ ID NO 13
<211> LENGTH: 43
<212> TYPE: DNA
<213> ORGANISM: Artificial Sequence
<220> FEATURE:
<223> OTHER INFORMATION: R558A SD F

<400> SEQUENCE: 13
aggaatacaa ccagcacgcc gcaacctcgg gcgacgatgc aga                    43

<210> SEQ ID NO 14
<211> LENGTH: 43
<212> TYPE: DNA
<213> ORGANISM: Artificial Sequence
<220> FEATURE:
<223> OTHER INFORMATION: R558A SD R

<400> SEQUENCE: 14
tctgcatcgt cgcccgaggt tgcggcgtgc tggttgtatt cct          43

<210> SEQ ID NO 15
<211> LENGTH: 43
<212> TYPE: DNA
<213> ORGANISM: Artificial Sequence
<220> FEATURE:
<223> OTHER INFORMATION: R558Q SD F

<400> SEQUENCE: 15
aggaatacaa ccagcacgcc cagacctcgg gcgacgatgc aga          43

<210> SEQ ID NO 16
<211> LENGTH: 43
<212> TYPE: DNA
<213> ORGANISM: Artificial Sequence
<220> FEATURE:
<223> OTHER INFORMATION: R558Q SD R

<400> SEQUENCE: 16
tctgcatcgt cgcccgaggt ctgggcgtgc tggttgtatt cct          43

<210> SEQ ID NO 17
<211> LENGTH: 43
<212> TYPE: DNA
<213> ORGANISM: Artificial Sequence
<220> FEATURE:
<223> OTHER INFORMATION: G561R SD F

<400> SEQUENCE: 17
accagcacgc ccgcacctcg cgcgacgatg cagaagcagc cgc          43

<210> SEQ ID NO 18
<211> LENGTH: 43
<212> TYPE: DNA
<213> ORGANISM: Artificial Sequence
<220> FEATURE:
<223> OTHER INFORMATION: G561R SD R

<400> SEQUENCE: 18
gcggctgctt ctgcatcgtc gcgcgaggtg cgggcgtgct ggt          43

<210> SEQ ID NO 19
<211> LENGTH: 43
<212> TYPE: DNA
<213> ORGANISM: Artificial Sequence
<220> FEATURE:
<223> OTHER INFORMATION: G561Y SD F

<400> SEQUENCE: 19
accagcacgc ccgcacctcg tacgacgatg cagaagcagc cgc          43

<210> SEQ ID NO 20
<211> LENGTH: 43
<212> TYPE: DNA
<213> ORGANISM: Artificial Sequence
<220> FEATURE:
<223> OTHER INFORMATION: G561Y SD R

<400> SEQUENCE: 20
gcggctgctt ctgcatcgtc gtacgaggtg cgggcgtgct ggt          43

<210> SEQ ID NO 21
<211> LENGTH: 616
<212> TYPE: PRT
<213> ORGANISM: Artificial Sequence

<220> FEATURE:
<223> OTHER INFORMATION: R558H AA

<400> SEQUENCE: 21

```
Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
            20                  25                  30

Gly Ser Ser Met Pro Val Asn Arg Tyr Met Pro Phe Glu Val Glu Val
        35                  40                  45

Glu Asp Ile Ser Leu Pro Asp Arg Thr Trp Pro Asp Lys Lys Ile Thr
    50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Arg Met Phe Glu Leu
                85                  90                  95

Leu Val Gln Met Gly Phe Lys Glu Ile Glu Val Gly Phe Pro Ser Ala
            100                 105                 110

Ser Gln Thr Asp Phe Asp Phe Val Arg Glu Ile Ile Glu Lys Asp Met
        115                 120                 125

Ile Pro Asp Asp Val Thr Ile Gln Val Leu Val Gln Ala Arg Glu His
    130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
            180                 185                 190

Leu Ile Lys Thr Val Ala Gln Asp Tyr Pro Asp Thr Asn Trp Arg Trp
        195                 200                 205

Gln Tyr Ser Pro Glu Ser Phe Thr Gly Thr Glu Val Glu Tyr Ala Lys
    210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                245                 250                 255

Val Tyr Ala Asp Ser Ile Glu Trp Met His Arg Asn Leu Asn Arg Arg
            260                 265                 270

Asp Ser Ile Ile Leu Ser Leu His Pro His Asn Asp Arg Gly Thr Gly
        275                 280                 285

Val Gly Ala Ala Glu Leu Gly Tyr Met Ala Gly Ala Asp Arg Ile Glu
    290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
                325                 330                 335

Phe Thr Asp Ile Arg Gln Ile Arg Ser Thr Val Glu Tyr Cys Asn Gln
            340                 345                 350

Leu Arg Val Pro Glu Arg His Pro Tyr Gly Gly Asp Leu Val Phe Thr
        355                 360                 365

Ala Phe Ser Gly Ser His Gln Asp Ala Val Asn Lys Gly Leu Asp Ala
    370                 375                 380

Met Ala Ala Lys Val Gln Pro Gly Ala Ser Ser Thr Glu Val Ser Trp
385                 390                 395                 400
```

Glu Gln Leu Arg Asp Thr Glu Trp Glu Val Pro Tyr Leu Pro Ile Asp
                405                 410                 415

Pro Lys Asp Val Gly Arg Asp Tyr Glu Ala Val Ile Arg Val Asn Ser
            420                 425                 430

Gln Ser Gly Lys Gly Gly Val Ala Tyr Ile Met Lys Thr Asp His Gly
        435                 440                 445

Leu Gln Ile Pro Arg Ser Met Gln Val Glu Phe Ser Thr Val Val Gln
    450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
            500                 505                 510

Ile Thr Ala Glu Leu Ile His Asn Gly Lys Asp Val Thr Val Asp Gly
        515                 520                 525

His Gly Asn Gly Pro Leu Ala Ala Tyr Ala Asn Ala Leu Glu Lys Leu
    530                 535                 540

Gly Ile Asp Val Glu Ile Gln Glu Tyr Asn Gln His Ala His Thr Ser
545                 550                 555                 560

Gly Asp Asp Ala Glu Ala Ala Tyr Val Leu Ala Glu Val Asn Gly
                565                 570                 575

Arg Lys Val Trp Gly Val Gly Ile Ala Gly Ser Ile Thr Tyr Ala Ser
            580                 585                 590

Leu Lys Ala Val Thr Ser Ala Val Asn Arg Ala Leu Asp Val Asn His
        595                 600                 605

Glu Ala Val Leu Ala Gly Gly Val
    610                 615

<210> SEQ ID NO 22
<211> LENGTH: 616
<212> TYPE: PRT
<213> ORGANISM: Artificial Sequence
<220> FEATURE:
<223> OTHER INFORMATION: R558A AA

<400> SEQUENCE: 22

Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
            20                  25                  30

Gly Ser Ser Met Pro Val Asn Arg Tyr Met Pro Phe Glu Val Glu Val
        35                  40                  45

Glu Asp Ile Ser Leu Pro Asp Arg Thr Trp Pro Asp Lys Lys Ile Thr
    50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Arg Met Phe Glu Leu
                85                  90                  95

Leu Val Gln Met Gly Phe Lys Glu Ile Glu Val Gly Phe Pro Ser Ala
            100                 105                 110

Ser Gln Thr Asp Phe Asp Phe Val Arg Glu Ile Ile Glu Lys Asp Met
        115                 120                 125

Ile Pro Asp Asp Val Thr Ile Gln Val Leu Val Gln Ala Arg Glu His
    130                 135                 140

```
Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
            180                 185                 190

Leu Ile Lys Thr Val Ala Gln Asp Tyr Pro Asp Thr Asn Trp Arg Trp
        195                 200                 205

Gln Tyr Ser Pro Glu Ser Phe Thr Gly Thr Glu Val Glu Tyr Ala Lys
    210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                245                 250                 255

Val Tyr Ala Asp Ser Ile Glu Trp Met His Arg Asn Leu Asn Arg Arg
                260                 265                 270

Asp Ser Ile Ile Leu Ser Leu His Pro His Asn Asp Arg Gly Thr Gly
            275                 280                 285

Val Gly Ala Ala Glu Leu Gly Tyr Met Ala Gly Ala Asp Arg Ile Glu
        290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
                325                 330                 335

Phe Thr Asp Ile Arg Gln Ile Arg Ser Thr Val Glu Tyr Cys Asn Gln
                340                 345                 350

Leu Arg Val Pro Glu Arg His Pro Tyr Gly Gly Asp Leu Val Phe Thr
            355                 360                 365

Ala Phe Ser Gly Ser His Gln Asp Ala Val Asn Lys Gly Leu Asp Ala
    370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
                405                 410                 415

Pro Lys Asp Val Gly Arg Asp Tyr Glu Ala Val Ile Arg Val Asn Ser
            420                 425                 430

Gln Ser Gly Lys Gly Gly Val Ala Tyr Ile Met Lys Thr Asp His Gly
        435                 440                 445

Leu Gln Ile Pro Arg Ser Met Gln Val Glu Phe Ser Thr Val Val Gln
    450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
            500                 505                 510

Ile Thr Ala Glu Leu Ile His Asn Gly Lys Asp Val Thr Val Asp Gly
        515                 520                 525

His Gly Asn Gly Pro Leu Ala Ala Tyr Ala Asn Ala Leu Glu Lys Leu
    530                 535                 540

Gly Ile Asp Val Glu Ile Gln Glu Tyr Asn Gln His Ala Ala Thr Ser
545                 550                 555                 560
```

Gly Asp Asp Ala Glu Ala Ala Tyr Val Leu Ala Glu Val Asn Gly
             565                 570                 575

Arg Lys Val Trp Gly Val Gly Ile Ala Gly Ser Ile Thr Tyr Ala Ser
         580                 585                 590

Leu Lys Ala Val Thr Ser Ala Val Asn Arg Ala Leu Asp Val Asn His
     595                 600                 605

Glu Ala Val Leu Ala Gly Gly Val
    610                 615

<210> SEQ ID NO 23
<211> LENGTH: 616
<212> TYPE: PRT
<213> ORGANISM: Artificial Sequence
<220> FEATURE:
<223> OTHER INFORMATION: R558Q AA

<400> SEQUENCE: 23

Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
            20                  25                  30

Gly Ser Ser Met Pro Val Asn Arg Tyr Met Pro Phe Glu Val Glu Val
        35                  40                  45

Glu Asp Ile Ser Leu Pro Asp Arg Thr Trp Pro Asp Lys Lys Ile Thr
    50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Arg Met Phe Glu Leu
                85                  90                  95

Leu Val Gln Met Gly Phe Lys Glu Ile Glu Val Gly Phe Pro Ser Ala
            100                 105                 110

Ser Gln Thr Asp Phe Asp Phe Val Arg Glu Ile Ile Glu Lys Asp Met
        115                 120                 125

Ile Pro Asp Asp Val Thr Ile Gln Val Leu Val Gln Ala Arg Glu His
    130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
            180                 185                 190

Leu Ile Lys Thr Val Ala Gln Asp Tyr Pro Asp Thr Asn Trp Arg Trp
        195                 200                 205

Gln Tyr Ser Pro Glu Ser Phe Thr Gly Thr Glu Val Glu Tyr Ala Lys
    210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                245                 250                 255

Val Tyr Ala Asp Ser Ile Glu Trp Met His Arg Asn Leu Asn Arg Arg
            260                 265                 270

Asp Ser Ile Ile Leu Ser Leu His Pro His Asn Asp Arg Gly Thr Gly
        275                 280                 285

Val Gly Ala Ala Glu Leu Gly Tyr Met Ala Gly Ala Asp Arg Ile Glu
    290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
            325                 330                 335

Phe Thr Asp Ile Arg Gln Ile Arg Ser Thr Val Glu Tyr Cys Asn Gln
            340                 345                 350

Leu Arg Val Pro Glu Arg His Pro Tyr Gly Gly Asp Leu Val Phe Thr
            355                 360                 365

Ala Phe Ser Gly Ser His Gln Asp Ala Val Asn Lys Gly Leu Asp Ala
        370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
            405                 410                 415

Pro Lys Asp Val Gly Arg Asp Tyr Glu Ala Val Ile Arg Val Asn Ser
            420                 425                 430

Gln Ser Gly Lys Gly Gly Val Ala Tyr Ile Met Lys Thr Asp His Gly
        435                 440                 445

Leu Gln Ile Pro Arg Ser Met Gln Val Glu Phe Ser Thr Val Val Gln
450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
            485                 490                 495

Ile Ala Leu Arg Val Glu Asn Ala Gln Thr Glu Asn Glu Asp Ala Ser
            500                 505                 510

Ile Thr Ala Glu Leu Ile His Asn Gly Lys Asp Val Thr Val Asp Gly
        515                 520                 525

His Gly Asn Gly Pro Leu Ala Ala Tyr Ala Asn Ala Leu Glu Lys Leu
            530                 535                 540

Gly Ile Asp Val Glu Ile Gln Glu Tyr Asn Gln His Ala Gln Thr Ser
545                 550                 555                 560

Gly Asp Asp Ala Glu Ala Ala Tyr Val Leu Ala Glu Val Asn Gly
            565                 570                 575

Arg Lys Val Trp Gly Val Gly Ile Ala Gly Ser Ile Thr Tyr Ala Ser
            580                 585                 590

Leu Lys Ala Val Thr Ser Ala Val Asn Arg Ala Leu Asp Val Asn His
        595                 600                 605

Glu Ala Val Leu Ala Gly Gly Val
610                 615

<210> SEQ ID NO 24
<211> LENGTH: 616
<212> TYPE: PRT
<213> ORGANISM: Artificial Sequence
<220> FEATURE:
<223> OTHER INFORMATION: G561D AA

<400> SEQUENCE: 24

Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
            20                  25                  30

Gly Ser Ser Met Pro Val Asn Arg Tyr Met Pro Phe Glu Val Glu Val
        35                  40                  45

-continued

```
Glu Asp Ile Ser Leu Pro Asp Arg Thr Trp Pro Asp Lys Lys Ile Thr
 50                  55                  60
Val Ala Pro Gln Trp Cys Ala Val Asp Leu Arg Asp Gly Asn Gln Ala
 65                  70                  75                  80
Leu Ile Asp Pro Met Ser Pro Glu Arg Lys Arg Met Phe Glu Leu
                 85                  90                  95
Leu Val Gln Met Gly Phe Lys Glu Ile Glu Val Gly Phe Pro Ser Ala
                100                 105                 110
Ser Gln Thr Asp Phe Asp Phe Val Arg Glu Ile Ile Glu Lys Asp Met
                115                 120                 125
Ile Pro Asp Asp Val Thr Ile Gln Val Leu Val Gln Ala Arg Glu His
130                 135                 140
Leu Ile Arg Arg Thr Phe Glu Ala Cys Glu Gly Ala Lys Asn Val Ile
145                 150                 155                 160
Val His Phe Tyr Asn Ser Thr Ser Ile Leu Gln Arg Asn Val Val Phe
                165                 170                 175
Arg Met Asp Lys Val Gln Val Lys Lys Leu Ala Thr Asp Ala Ala Glu
                180                 185                 190
Leu Ile Lys Thr Val Ala Gln Asp Tyr Pro Asp Thr Asn Trp Arg Trp
                195                 200                 205
Gln Tyr Ser Pro Glu Ser Phe Thr Gly Thr Glu Val Glu Tyr Ala Lys
210                 215                 220
Glu Val Val Asp Ala Val Glu Val Met Asp Pro Thr Pro Glu Asn
225                 230                 235                 240
Pro Met Ile Ile Asn Leu Pro Ser Thr Val Glu Met Ile Thr Pro Asn
                245                 250                 255
Val Tyr Ala Asp Ser Ile Glu Trp Met His Arg Asn Leu Asn Arg Arg
                260                 265                 270
Asp Ser Ile Ile Leu Ser Leu His Pro His Asn Asp Arg Gly Thr Gly
                275                 280                 285
Val Gly Ala Ala Glu Leu Gly Tyr Met Ala Gly Ala Asp Arg Ile Glu
290                 295                 300
Gly Cys Leu Phe Gly Asn Gly Glu Arg Thr Gly Asn Val Cys Leu Val
305                 310                 315                 320
Thr Leu Ala Leu Asn Met Leu Thr Gln Gly Val Asp Pro Gln Leu Asp
                325                 330                 335
Phe Thr Asp Ile Arg Gln Ile Arg Ser Thr Val Glu Tyr Cys Asn Gln
                340                 345                 350
Leu Arg Val Pro Glu Arg His Pro Tyr Gly Gly Asp Leu Val Phe Thr
                355                 360                 365
Ala Phe Ser Gly Ser His Gln Asp Ala Val Asn Lys Gly Leu Asp Ala
370                 375                 380
Met Ala Ala Lys Val Gln Pro Gly Ala Ser Ser Thr Glu Val Ser Trp
385                 390                 395                 400
Glu Gln Leu Arg Asp Thr Glu Trp Glu Val Pro Tyr Leu Pro Ile Asp
                405                 410                 415
Pro Lys Asp Val Gly Arg Asp Tyr Glu Ala Val Ile Arg Val Asn Ser
                420                 425                 430
Gln Ser Gly Lys Gly Gly Val Ala Tyr Ile Met Lys Thr Asp His Gly
                435                 440                 445
Leu Gln Ile Pro Arg Ser Met Gln Val Glu Phe Ser Thr Val Val Gln
450                 455                 460
Asn Val Thr Asp Ala Glu Gly Gly Glu Val Asn Ser Lys Ala Met Trp
```

```
            465                 470                 475                 480
Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
                500                 505                 510

Ile Thr Ala Glu Leu Ile His Asn Gly Lys Asp Val Thr Val Asp Gly
                515                 520                 525

His Gly Asn Gly Pro Leu Ala Ala Tyr Ala Asn Ala Leu Glu Lys Leu
                530                 535                 540

Gly Ile Asp Val Glu Ile Gln Glu Tyr Asn Gln His Ala Arg Thr Ser
545                 550                 555                 560

Asp Asp Asp Ala Glu Ala Ala Tyr Val Leu Ala Glu Val Asn Asn Gly
                565                 570                 575

Arg Lys Val Trp Gly Val Gly Ile Ala Gly Ser Ile Thr Tyr Ala Ser
                580                 585                 590

Leu Lys Ala Val Thr Ser Ala Val Asn Arg Ala Leu Asp Val Asn His
                595                 600                 605

Glu Ala Val Leu Ala Gly Gly Val
                610                 615

<210> SEQ ID NO 25
<211> LENGTH: 616
<212> TYPE: PRT
<213> ORGANISM: Artificial Sequence
<220> FEATURE:
<223> OTHER INFORMATION: G561R AA

<400> SEQUENCE: 25

Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
                20                  25                  30

Gly Ser Ser Met Pro Val Asn Arg Tyr Met Pro Phe Glu Val Glu Val
                35                  40                  45

Glu Asp Ile Ser Leu Pro Asp Arg Thr Trp Pro Asp Lys Lys Ile Thr
50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Arg Met Phe Glu Leu
                85                  90                  95

Leu Val Gln Met Gly Phe Lys Glu Ile Glu Val Gly Phe Pro Ser Ala
                100                 105                 110

Ser Gln Thr Asp Phe Asp Phe Val Arg Glu Ile Ile Glu Lys Asp Met
                115                 120                 125

Ile Pro Asp Asp Val Thr Ile Gln Val Leu Val Gln Ala Arg Glu His
                130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
                180                 185                 190

Leu Ile Lys Thr Val Ala Gln Asp Tyr Pro Asp Thr Asn Trp Arg Trp
                195                 200                 205

Gln Tyr Ser Pro Glu Ser Phe Thr Gly Thr Glu Val Glu Tyr Ala Lys
```

```
            210                 215                 220
Glu Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                245                 250                 255

Val Tyr Ala Asp Ser Ile Glu Trp Met His Arg Asn Leu Asn Arg Arg
            260                 265                 270

Asp Ser Ile Ile Leu Ser Leu His Pro His Asn Asp Arg Gly Thr Gly
        275                 280                 285

Val Gly Ala Ala Glu Leu Gly Tyr Met Ala Gly Ala Asp Arg Ile Glu
    290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
                325                 330                 335

Phe Thr Asp Ile Arg Gln Ile Arg Ser Thr Val Glu Tyr Cys Asn Gln
            340                 345                 350

Leu Arg Val Pro Glu Arg His Pro Tyr Gly Gly Asp Leu Val Phe Thr
        355                 360                 365

Ala Phe Ser Gly Ser His Gln Asp Ala Val Asn Lys Gly Leu Asp Ala
    370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
                405                 410                 415

Pro Lys Asp Val Gly Arg Asp Tyr Glu Ala Val Ile Arg Val Asn Ser
            420                 425                 430

Gln Ser Gly Lys Gly Gly Val Ala Tyr Ile Met Lys Thr Asp His Gly
        435                 440                 445

Leu Gln Ile Pro Arg Ser Met Gln Val Glu Phe Ser Thr Val Val Gln
    450                 455                 460

Asn Val Thr Asp Ala Glu Gly Gly Val Asn Ser Lys Ala Met Trp
465                 470                 475                 480

Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
            500                 505                 510

Ile Thr Ala Glu Leu Ile His Asn Gly Lys Asp Val Thr Val Asp Gly
        515                 520                 525

His Gly Asn Gly Pro Leu Ala Ala Tyr Ala Asn Ala Leu Glu Lys Leu
    530                 535                 540

Gly Ile Asp Val Glu Ile Gln Glu Tyr Asn Gln His Ala Arg Thr Ser
545                 550                 555                 560

Arg Asp Asp Ala Glu Ala Ala Tyr Val Leu Ala Glu Val Asn Gly
                565                 570                 575

Arg Lys Val Trp Gly Val Gly Ile Ala Gly Ser Ile Thr Tyr Ala Ser
            580                 585                 590

Leu Lys Ala Val Thr Ser Ala Val Asn Arg Ala Leu Asp Val Asn His
        595                 600                 605

Glu Ala Val Leu Ala Gly Gly Val
    610                 615

<210> SEQ ID NO 26
```

<211> LENGTH: 616
<212> TYPE: PRT
<213> ORGANISM: Artificial Sequence
<220> FEATURE:
<223> OTHER INFORMATION: G561Y AA

<400> SEQUENCE: 26

```
Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
            20                  25                  30

Gly Ser Ser Met Pro Val Asn Arg Tyr Met Pro Phe Glu Val Glu Val
        35                  40                  45

Glu Asp Ile Ser Leu Pro Asp Arg Thr Trp Pro Asp Lys Lys Ile Thr
50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Met Phe Glu Leu
                85                  90                  95

Leu Val Gln Met Gly Phe Lys Glu Ile Glu Val Gly Phe Pro Ser Ala
                100                 105                 110

Ser Gln Thr Asp Phe Asp Phe Val Arg Glu Ile Ile Glu Lys Asp Met
            115                 120                 125

Ile Pro Asp Asp Val Thr Ile Gln Val Leu Val Gln Ala Arg Glu His
130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
                180                 185                 190

Leu Ile Lys Thr Val Ala Gln Asp Tyr Pro Asp Thr Asn Trp Arg Trp
            195                 200                 205

Gln Tyr Ser Pro Glu Ser Phe Thr Gly Thr Glu Val Glu Tyr Ala Lys
210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                245                 250                 255

Val Tyr Ala Asp Ser Ile Glu Trp Met His Arg Asn Leu Asn Arg Arg
                260                 265                 270

Asp Ser Ile Ile Leu Ser Leu His Pro His Asn Asp Arg Gly Thr Gly
            275                 280                 285

Val Gly Ala Ala Glu Leu Gly Tyr Met Ala Gly Ala Asp Arg Ile Glu
290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
                325                 330                 335

Phe Thr Asp Ile Arg Gln Ile Arg Ser Thr Val Glu Tyr Cys Asn Gln
                340                 345                 350

Leu Arg Val Pro Glu Arg His Pro Tyr Gly Gly Asp Leu Val Phe Thr
            355                 360                 365

Ala Phe Ser Gly Ser His Gln Asp Ala Val Asn Lys Gly Leu Asp Ala
370                 375                 380
```

```
Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
            405                 410                 415

Pro Lys Asp Val Gly Arg Asp Tyr Glu Ala Val Ile Arg Val Asn Ser
        420                 425                 430

Gln Ser Gly Lys Gly Val Ala Tyr Ile Met Lys Thr Asp His Gly
            435                 440                 445

Leu Gln Ile Pro Arg Ser Met Gln Val Glu Phe Ser Thr Val Val Gln
    450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
            485                 490                 495

Ile Ala Leu Arg Val Glu Asn Ala Gln Thr Glu Asn Glu Asp Ala Ser
        500                 505                 510

Ile Thr Ala Glu Leu Ile His Asn Gly Lys Asp Val Thr Val Asp Gly
        515                 520                 525

His Gly Asn Gly Pro Leu Ala Ala Tyr Ala Asn Ala Leu Glu Lys Leu
    530                 535                 540

Gly Ile Asp Val Glu Ile Gln Glu Tyr Asn Gln His Ala Arg Thr Ser
545                 550                 555                 560

Tyr Asp Asp Ala Glu Ala Ala Tyr Val Leu Ala Glu Val Asn Gly
            565                 570                 575

Arg Lys Val Trp Gly Val Gly Ile Ala Gly Ser Ile Thr Tyr Ala Ser
            580                 585                 590

Leu Lys Ala Val Thr Ser Ala Val Asn Arg Ala Leu Asp Val Asn His
        595                 600                 605

Glu Ala Val Leu Ala Gly Gly Val
    610                 615

<210> SEQ ID NO 27
<211> LENGTH: 616
<212> TYPE: PRT
<213> ORGANISM: Artificial Sequence
<220> FEATURE:
<223> OTHER INFORMATION: R558H, G561D AA

<400> SEQUENCE: 27

Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
            20                  25                  30

Gly Ser Ser Met Pro Val Asn Arg Tyr Met Pro Phe Glu Val Glu Val
        35                  40                  45

Glu Asp Ile Ser Leu Pro Asp Arg Thr Trp Pro Asp Lys Lys Ile Thr
    50                  55                  60

Val Ala Pro Gln Trp Cys Ala Val Asp Leu Arg Asp Gly Asn Gln Ala
65              70                  75                  80

Leu Ile Asp Pro Met Ser Pro Glu Arg Lys Arg Arg Met Phe Glu Leu
            85                  90                  95

Leu Val Gln Met Gly Phe Lys Glu Ile Glu Val Gly Phe Pro Ser Ala
            100                 105                 110

Ser Gln Thr Asp Phe Asp Phe Val Arg Glu Ile Ile Glu Lys Asp Met
        115                 120                 125
```

```
Ile Pro Asp Asp Val Thr Ile Gln Val Leu Val Gln Ala Arg Glu His
130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
            180                 185                 190

Leu Ile Lys Thr Val Ala Gln Asp Tyr Pro Asp Thr Asn Trp Arg Trp
        195                 200                 205

Gln Tyr Ser Pro Glu Ser Phe Thr Gly Thr Glu Val Glu Tyr Ala Lys
    210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                245                 250                 255

Val Tyr Ala Asp Ser Ile Glu Trp Met His Arg Asn Leu Asn Arg Arg
            260                 265                 270

Asp Ser Ile Ile Leu Ser Leu His Pro His Asn Asp Arg Gly Thr Gly
        275                 280                 285

Val Gly Ala Ala Glu Leu Gly Tyr Met Ala Gly Ala Asp Arg Ile Glu
    290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
                325                 330                 335

Phe Thr Asp Ile Arg Gln Ile Arg Ser Thr Val Glu Tyr Cys Asn Gln
            340                 345                 350

Leu Arg Val Pro Glu Arg His Pro Tyr Gly Gly Asp Leu Val Phe Thr
        355                 360                 365

Ala Phe Ser Gly Ser His Gln Asp Ala Val Asn Lys Gly Leu Asp Ala
    370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
                405                 410                 415

Pro Lys Asp Val Gly Arg Asp Tyr Glu Ala Val Ile Arg Val Asn Ser
            420                 425                 430

Gln Ser Gly Lys Gly Val Ala Tyr Ile Met Lys Thr Asp His Gly
        435                 440                 445

Leu Gln Ile Pro Arg Ser Met Gln Val Glu Phe Ser Thr Val Val Gln
    450                 455                 460

Asn Val Thr Asp Ala Glu Gly Gly Val Asn Ser Lys Ala Met Trp
465                 470                 475                 480

Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
            500                 505                 510

Ile Thr Ala Glu Leu Ile His Asn Gly Lys Asp Val Thr Val Asp Gly
        515                 520                 525

His Gly Asn Gly Pro Leu Ala Ala Tyr Ala Asn Ala Leu Glu Lys Leu
    530                 535                 540
```

```
Gly Ile Asp Val Glu Ile Gln Glu Tyr Asn Gln His Ala His Thr Ser
545                 550                 555                 560

Asp Asp Asp Ala Glu Ala Ala Tyr Val Leu Ala Glu Val Asn Gly
            565                 570                 575

Arg Lys Val Trp Gly Val Gly Ile Ala Gly Ser Ile Thr Tyr Ala Ser
            580                 585                 590

Leu Lys Ala Val Thr Ser Ala Val Asn Arg Ala Leu Asp Val Asn His
        595                 600                 605

Glu Ala Val Leu Ala Gly Gly Val
    610                 615
```

<210> SEQ ID NO 28
<211> LENGTH: 616
<212> TYPE: PRT
<213> ORGANISM: Artificial Sequence
<220> FEATURE:
<223> OTHER INFORMATION: R558H, G561R AA

<400> SEQUENCE: 28

```
Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
            20                  25                  30

Gly Ser Ser Met Pro Val Asn Arg Tyr Met Pro Phe Glu Val Glu Val
        35                  40                  45

Glu Asp Ile Ser Leu Pro Asp Arg Thr Trp Pro Asp Lys Lys Ile Thr
    50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Arg Met Phe Glu Leu
                85                  90                  95

Leu Val Gln Met Gly Phe Lys Glu Ile Glu Val Gly Phe Pro Ser Ala
            100                 105                 110

Ser Gln Thr Asp Phe Asp Phe Val Arg Glu Ile Ile Glu Lys Asp Met
        115                 120                 125

Ile Pro Asp Asp Val Thr Ile Gln Val Leu Val Gln Ala Arg Glu His
    130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
            180                 185                 190

Leu Ile Lys Thr Val Ala Gln Asp Tyr Pro Asp Thr Asn Trp Arg Trp
        195                 200                 205

Gln Tyr Ser Pro Glu Ser Phe Thr Gly Thr Glu Val Glu Tyr Ala Lys
    210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                245                 250                 255

Val Tyr Ala Asp Ser Ile Glu Trp Met His Arg Asn Leu Asn Arg Arg
            260                 265                 270

Asp Ser Ile Ile Leu Ser Leu His Pro His Asn Asp Arg Gly Thr Gly
        275                 280                 285
```

```
Val Gly Ala Ala Glu Leu Gly Tyr Met Ala Gly Ala Asp Arg Ile Glu
    290                 295                 300
Gly Cys Leu Phe Gly Asn Gly Glu Arg Thr Gly Asn Val Cys Leu Val
305                 310                 315                 320
Thr Leu Ala Leu Asn Met Leu Thr Gln Gly Val Asp Pro Gln Leu Asp
                325                 330                 335
Phe Thr Asp Ile Arg Gln Ile Arg Ser Thr Val Glu Tyr Cys Asn Gln
            340                 345                 350
Leu Arg Val Pro Glu Arg His Pro Tyr Gly Gly Asp Leu Val Phe Thr
        355                 360                 365
Ala Phe Ser Gly Ser His Gln Asp Ala Val Asn Lys Gly Leu Asp Ala
    370                 375                 380
Met Ala Lys Val Gln Pro Gly Ala Ser Ser Thr Glu Val Ser Trp
385                 390                 395                 400
Glu Gln Leu Arg Asp Thr Glu Trp Glu Val Pro Tyr Leu Pro Ile Asp
                405                 410                 415
Pro Lys Asp Val Gly Arg Asp Tyr Glu Ala Val Ile Arg Val Asn Ser
            420                 425                 430
Gln Ser Gly Lys Gly Val Ala Tyr Ile Met Lys Thr Asp His Gly
        435                 440                 445
Leu Gln Ile Pro Arg Ser Met Gln Val Glu Phe Ser Thr Val Val Gln
    450                 455                 460
Asn Val Thr Asp Ala Glu Gly Gly Val Asn Ser Lys Ala Met Trp
465                 470                 475                 480
Asp Ile Phe Ala Thr Glu Tyr Leu Glu Arg Thr Ala Pro Val Glu Gln
                485                 490                 495
Ile Ala Leu Arg Val Glu Asn Ala Gln Thr Glu Asn Glu Asp Ala Ser
            500                 505                 510
Ile Thr Ala Glu Leu Ile His Asn Gly Lys Asp Val Thr Val Asp Gly
        515                 520                 525
His Gly Asn Gly Pro Leu Ala Ala Tyr Ala Asn Ala Leu Glu Lys Leu
    530                 535                 540
Gly Ile Asp Val Glu Ile Gln Glu Tyr Asn Gln His Ala His Thr Ser
545                 550                 555                 560
Arg Asp Asp Ala Glu Ala Ala Tyr Val Leu Ala Glu Val Asn Gly
                565                 570                 575
Arg Lys Val Trp Gly Val Gly Ile Ala Gly Ser Ile Thr Tyr Ala Ser
            580                 585                 590
Leu Lys Ala Val Thr Ser Ala Val Asn Arg Ala Leu Asp Val Asn His
        595                 600                 605
Glu Ala Val Leu Ala Gly Gly Val
    610                 615

<210> SEQ ID NO 29
<211> LENGTH: 616
<212> TYPE: PRT
<213> ORGANISM: Artificial Sequence
<220> FEATURE:
<223> OTHER INFORMATION: R558H, G561Y AA

<400> SEQUENCE: 29

Met Ser Pro Asn Asp Ala Phe Ile Ser Ala Pro Ala Lys Ile Glu Thr
1               5                   10                  15
Pro Val Gly Pro Arg Asn Glu Gly Gln Pro Ala Trp Asn Lys Gln Arg
            20                  25                  30
```

-continued

```
Gly Ser Ser Met Pro Val Asn Arg Tyr Met Pro Phe Glu Val
        35                  40                  45
Glu Asp Ile Ser Leu Pro Asp Arg Thr Trp Pro Asp Lys Lys Ile Thr
 50                  55                  60
Val Ala Pro Gln Trp Cys Ala Val Asp Leu Arg Asp Gly Asn Gln Ala
 65                  70                  75                  80
Leu Ile Asp Pro Met Ser Pro Glu Arg Lys Arg Arg Met Phe Glu Leu
                 85                  90                  95
Leu Val Gln Met Gly Phe Lys Glu Ile Glu Val Gly Phe Pro Ser Ala
            100                 105                 110
Ser Gln Thr Asp Phe Asp Phe Val Arg Glu Ile Ile Glu Lys Asp Met
        115                 120                 125
Ile Pro Asp Asp Val Thr Ile Gln Val Leu Val Gln Ala Arg Glu His
    130                 135                 140
Leu Ile Arg Arg Thr Phe Glu Ala Cys Glu Gly Ala Lys Asn Val Ile
145                 150                 155                 160
Val His Phe Tyr Asn Ser Thr Ser Ile Leu Gln Arg Asn Val Val Phe
                165                 170                 175
Arg Met Asp Lys Val Gln Val Lys Lys Leu Ala Thr Asp Ala Ala Glu
            180                 185                 190
Leu Ile Lys Thr Val Ala Gln Asp Tyr Pro Asp Thr Asn Trp Arg Trp
        195                 200                 205
Gln Tyr Ser Pro Glu Ser Phe Thr Gly Thr Glu Val Glu Tyr Ala Lys
    210                 215                 220
Glu Val Val Asp Ala Val Val Glu Val Met Asp Pro Thr Pro Glu Asn
225                 230                 235                 240
Pro Met Ile Ile Asn Leu Pro Ser Thr Val Glu Met Ile Thr Pro Asn
                245                 250                 255
Val Tyr Ala Asp Ser Ile Glu Trp Met His Arg Asn Leu Asn Arg Arg
            260                 265                 270
Asp Ser Ile Ile Leu Ser Leu His Pro His Asn Asp Arg Gly Thr Gly
        275                 280                 285
Val Gly Ala Ala Glu Leu Gly Tyr Met Ala Gly Ala Asp Arg Ile Glu
    290                 295                 300
Gly Cys Leu Phe Gly Asn Gly Glu Arg Thr Gly Asn Val Cys Leu Val
305                 310                 315                 320
Thr Leu Ala Leu Asn Met Leu Thr Gln Gly Val Asp Pro Gln Leu Asp
                325                 330                 335
Phe Thr Asp Ile Arg Gln Ile Arg Ser Thr Val Glu Tyr Cys Asn Gln
            340                 345                 350
Leu Arg Val Pro Glu Arg His Pro Tyr Gly Gly Asp Leu Val Phe Thr
        355                 360                 365
Ala Phe Ser Gly Ser His Gln Asp Ala Val Asn Lys Gly Leu Asp Ala
    370                 375                 380
Met Ala Ala Lys Val Gln Pro Gly Ala Ser Ser Thr Glu Val Ser Trp
385                 390                 395                 400
Glu Gln Leu Arg Asp Thr Glu Trp Glu Val Pro Tyr Leu Pro Ile Asp
                405                 410                 415
Pro Lys Asp Val Gly Arg Asp Tyr Glu Ala Val Ile Arg Val Asn Ser
            420                 425                 430
Gln Ser Gly Lys Gly Gly Val Ala Tyr Ile Met Lys Thr Asp His Gly
        435                 440                 445
Leu Gln Ile Pro Arg Ser Met Gln Val Glu Phe Ser Thr Val Val Gln
```

```
                    450                 455                 460
Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
                    485                 490                 495

Ile Ala Leu Arg Val Glu Asn Ala Gln Thr Glu Asn Glu Asp Ala Ser
                500                 505                 510

Ile Thr Ala Glu Leu Ile His Asn Gly Lys Asp Val Thr Val Asp Gly
            515                 520                 525

His Gly Asn Gly Pro Leu Ala Ala Tyr Ala Asn Ala Leu Glu Lys Leu
            530                 535                 540

Gly Ile Asp Val Glu Ile Gln Glu Tyr Asn Gln His Ala His Thr Ser
545                 550                 555                 560

Tyr Asp Asp Ala Glu Ala Ala Tyr Val Leu Ala Glu Val Asn Gly
                565                 570                 575

Arg Lys Val Trp Gly Val Gly Ile Ala Gly Ser Ile Thr Tyr Ala Ser
                580                 585                 590

Leu Lys Ala Val Thr Ser Ala Val Asn Arg Ala Leu Asp Val Asn His
            595                 600                 605

Glu Ala Val Leu Ala Gly Gly Val
            610                 615

<210> SEQ ID NO 30
<211> LENGTH: 616
<212> TYPE: PRT
<213> ORGANISM: Artificial Sequence
<220> FEATURE:
<223> OTHER INFORMATION: R558A, G561D AA

<400> SEQUENCE: 30

Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
                20                  25                  30

Gly Ser Ser Met Pro Val Asn Arg Tyr Met Pro Phe Glu Val Glu Val
            35                  40                  45

Glu Asp Ile Ser Leu Pro Asp Arg Thr Trp Pro Asp Lys Lys Ile Thr
50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Met Phe Glu Leu
                85                  90                  95

Leu Val Gln Met Gly Phe Lys Glu Ile Glu Val Gly Phe Pro Ser Ala
                100                 105                 110

Ser Gln Thr Asp Phe Asp Phe Val Arg Glu Ile Ile Glu Lys Asp Met
            115                 120                 125

Ile Pro Asp Asp Val Thr Ile Gln Val Leu Val Gln Ala Arg Glu His
            130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
            180                 185                 190

Leu Ile Lys Thr Val Ala Gln Asp Tyr Pro Asp Thr Asn Trp Arg Trp
```

```
            195                 200                 205
Gln Tyr Ser Pro Glu Ser Phe Thr Gly Thr Glu Val Glu Tyr Ala Lys
210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                245                 250                 255

Val Tyr Ala Asp Ser Ile Glu Trp Met His Arg Asn Leu Asn Arg Arg
                260                 265                 270

Asp Ser Ile Ile Leu Ser Leu His Pro His Asn Asp Arg Gly Thr Gly
                275                 280                 285

Val Gly Ala Ala Glu Leu Gly Tyr Met Ala Gly Ala Asp Arg Ile Glu
290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
                325                 330                 335

Phe Thr Asp Ile Arg Gln Ile Arg Ser Thr Val Glu Tyr Cys Asn Gln
                340                 345                 350

Leu Arg Val Pro Glu Arg His Pro Tyr Gly Gly Asp Leu Val Phe Thr
                355                 360                 365

Ala Phe Ser Gly Ser His Gln Asp Ala Val Asn Lys Gly Leu Asp Ala
370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
                405                 410                 415

Pro Lys Asp Val Gly Arg Asp Tyr Glu Ala Val Ile Arg Val Asn Ser
                420                 425                 430

Gln Ser Gly Lys Gly Val Ala Tyr Ile Met Lys Thr Asp His Gly
                435                 440                 445

Leu Gln Ile Pro Arg Ser Met Gln Val Glu Phe Ser Thr Val Val Gln
                450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
                500                 505                 510

Ile Thr Ala Glu Leu Ile His Asn Gly Lys Asp Val Thr Val Asp Gly
                515                 520                 525

His Gly Asn Gly Pro Leu Ala Ala Tyr Ala Asn Ala Leu Glu Lys Leu
530                 535                 540

Gly Ile Asp Val Glu Ile Gln Glu Tyr Asn Gln His Ala Ala Thr Ser
545                 550                 555                 560

Asp Asp Asp Ala Glu Ala Ala Tyr Val Leu Ala Glu Val Asn Gly
                565                 570                 575

Arg Lys Val Trp Gly Val Gly Ile Ala Gly Ser Ile Thr Tyr Ala Ser
                580                 585                 590

Leu Lys Ala Val Thr Ser Ala Val Asn Arg Ala Leu Asp Val Asn His
                595                 600                 605

Glu Ala Val Leu Ala Gly Gly Val
610                 615
```

<210> SEQ ID NO 31
<211> LENGTH: 616
<212> TYPE: PRT
<213> ORGANISM: Artificial Sequence
<220> FEATURE:
<223> OTHER INFORMATION: R558A, G561R AA

<400> SEQUENCE: 31

```
Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
                20                  25                  30

Gly Ser Ser Met Pro Val Asn Arg Tyr Met Pro Phe Glu Val Glu Val
            35                  40                  45

Glu Asp Ile Ser Leu Pro Asp Arg Thr Trp Pro Asp Lys Lys Ile Thr
    50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Arg Met Phe Glu Leu
                85                  90                  95

Leu Val Gln Met Gly Phe Lys Glu Ile Glu Val Gly Phe Pro Ser Ala
                100                 105                 110

Ser Gln Thr Asp Phe Asp Phe Val Arg Glu Ile Ile Glu Lys Asp Met
            115                 120                 125

Ile Pro Asp Asp Val Thr Ile Gln Val Leu Val Gln Ala Arg Glu His
    130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
                180                 185                 190

Leu Ile Lys Thr Val Ala Gln Asp Tyr Pro Asp Thr Asn Trp Arg Trp
            195                 200                 205

Gln Tyr Ser Pro Glu Ser Phe Thr Gly Thr Glu Val Glu Tyr Ala Lys
    210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                245                 250                 255

Val Tyr Ala Asp Ser Ile Glu Trp Met His Arg Asn Leu Asn Arg Arg
                260                 265                 270

Asp Ser Ile Ile Leu Ser Leu His Pro His Asn Asp Arg Gly Thr Gly
            275                 280                 285

Val Gly Ala Ala Glu Leu Gly Tyr Met Ala Gly Ala Asp Arg Ile Glu
    290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
                325                 330                 335

Phe Thr Asp Ile Arg Gln Ile Arg Ser Thr Val Glu Tyr Cys Asn Gln
                340                 345                 350

Leu Arg Val Pro Glu Arg His Pro Tyr Gly Gly Asp Leu Val Phe Thr
            355                 360                 365
```

```
Ala Phe Ser Gly Ser His Gln Asp Ala Val Asn Lys Gly Leu Asp Ala
    370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
                405                 410                 415

Pro Lys Asp Val Gly Arg Asp Tyr Glu Ala Val Ile Arg Val Asn Ser
                420                 425                 430

Gln Ser Gly Lys Gly Gly Val Ala Tyr Ile Met Lys Thr Asp His Gly
                435                 440                 445

Leu Gln Ile Pro Arg Ser Met Gln Val Glu Phe Ser Thr Val Val Gln
    450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
                500                 505                 510

Ile Thr Ala Glu Leu Ile His Asn Gly Lys Asp Val Thr Val Asp Gly
    515                 520                 525

His Gly Asn Gly Pro Leu Ala Ala Tyr Ala Asn Ala Leu Glu Lys Leu
    530                 535                 540

Gly Ile Asp Val Glu Ile Gln Glu Tyr Asn Gln His Ala Ala Thr Ser
545                 550                 555                 560

Arg Asp Asp Ala Glu Ala Ala Tyr Val Leu Ala Glu Val Asn Gly
                565                 570                 575

Arg Lys Val Trp Gly Val Gly Ile Ala Gly Ser Ile Thr Tyr Ala Ser
                580                 585                 590

Leu Lys Ala Val Thr Ser Ala Val Asn Arg Ala Leu Asp Val Asn His
                595                 600                 605

Glu Ala Val Leu Ala Gly Gly Val
    610                 615

<210> SEQ ID NO 32
<211> LENGTH: 616
<212> TYPE: PRT
<213> ORGANISM: Artificial Sequence
<220> FEATURE:
<223> OTHER INFORMATION: R558A, G561Y AA

<400> SEQUENCE: 32

Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
                20                  25                  30

Gly Ser Ser Met Pro Val Asn Arg Tyr Met Pro Phe Glu Val Glu Val
                35                  40                  45

Glu Asp Ile Ser Leu Pro Asp Arg Thr Trp Pro Asp Lys Lys Ile Thr
    50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Arg Met Phe Glu Leu
                85                  90                  95

Leu Val Gln Met Gly Phe Lys Glu Ile Glu Val Gly Phe Pro Ser Ala
                100                 105                 110
```

-continued

Ser Gln Thr Asp Phe Asp Phe Val Arg Glu Ile Ile Glu Lys Asp Met
        115                 120                 125

Ile Pro Asp Asp Val Thr Ile Gln Val Leu Val Gln Ala Arg Glu His
    130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
            165                 170                 175

Arg Met Asp Lys Val Gln Val Lys Lys Leu Ala Thr Asp Ala Ala Glu
                180                 185                 190

Leu Ile Lys Thr Val Ala Gln Asp Tyr Pro Asp Thr Asn Trp Arg Trp
        195                 200                 205

Gln Tyr Ser Pro Glu Ser Phe Thr Gly Thr Glu Val Glu Tyr Ala Lys
    210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
            245                 250                 255

Val Tyr Ala Asp Ser Ile Glu Trp Met His Arg Asn Leu Asn Arg Arg
                260                 265                 270

Asp Ser Ile Ile Leu Ser Leu His Pro His Asn Asp Arg Gly Thr Gly
        275                 280                 285

Val Gly Ala Ala Glu Leu Gly Tyr Met Ala Gly Ala Asp Arg Ile Glu
    290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
            325                 330                 335

Phe Thr Asp Ile Arg Gln Ile Arg Ser Thr Val Glu Tyr Cys Asn Gln
                340                 345                 350

Leu Arg Val Pro Glu Arg His Pro Tyr Gly Gly Asp Leu Val Phe Thr
        355                 360                 365

Ala Phe Ser Gly Ser His Gln Asp Ala Val Asn Lys Gly Leu Asp Ala
    370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
            405                 410                 415

Pro Lys Asp Val Gly Arg Asp Tyr Glu Ala Val Ile Arg Val Asn Ser
                420                 425                 430

Gln Ser Gly Lys Gly Gly Val Ala Tyr Ile Met Lys Thr Asp His Gly
        435                 440                 445

Leu Gln Ile Pro Arg Ser Met Gln Val Glu Phe Ser Thr Val Val Gln
    450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
            485                 490                 495

Ile Ala Leu Arg Val Glu Asn Ala Gln Thr Glu Asn Glu Asp Ala Ser
                500                 505                 510

Ile Thr Ala Glu Leu Ile His Asn Gly Lys Asp Val Thr Val Asp Gly
        515                 520                 525

```
His Gly Asn Gly Pro Leu Ala Ala Tyr Ala Asn Ala Leu Glu Lys Leu
        530                 535                 540

Gly Ile Asp Val Glu Ile Gln Glu Tyr Asn Gln His Ala Ala Thr Ser
545                 550                 555                 560

Tyr Asp Asp Ala Glu Ala Ala Tyr Val Leu Ala Glu Val Asn Gly
                565                 570                 575

Arg Lys Val Trp Gly Val Gly Ile Ala Gly Ser Ile Thr Tyr Ala Ser
                580                 585                 590

Leu Lys Ala Val Thr Ser Ala Val Asn Arg Ala Leu Asp Val Asn His
        595                 600                 605

Glu Ala Val Leu Ala Gly Gly Val
        610                 615
```

<210> SEQ ID NO 33
<211> LENGTH: 616
<212> TYPE: PRT
<213> ORGANISM: Artificial Sequence
<220> FEATURE:
<223> OTHER INFORMATION: R558Q, G561D AA

<400> SEQUENCE: 33

```
Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
                20                  25                  30

Gly Ser Ser Met Pro Val Asn Arg Tyr Met Pro Phe Glu Val Glu Val
            35                  40                  45

Glu Asp Ile Ser Leu Pro Asp Arg Thr Trp Pro Asp Lys Lys Ile Thr
    50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Arg Met Phe Glu Leu
                85                  90                  95

Leu Val Gln Met Gly Phe Lys Glu Ile Glu Val Gly Phe Pro Ser Ala
                100                 105                 110

Ser Gln Thr Asp Phe Asp Phe Val Arg Glu Ile Ile Glu Lys Asp Met
            115                 120                 125

Ile Pro Asp Asp Val Thr Ile Gln Val Leu Val Gln Ala Arg Glu His
    130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
                180                 185                 190

Leu Ile Lys Thr Val Ala Gln Asp Tyr Pro Asp Thr Asn Trp Arg Trp
            195                 200                 205

Gln Tyr Ser Pro Glu Ser Phe Thr Gly Thr Glu Val Glu Tyr Ala Lys
    210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                245                 250                 255

Val Tyr Ala Asp Ser Ile Glu Trp Met His Arg Asn Leu Asn Arg Arg
                260                 265                 270
```

```
Asp Ser Ile Ile Leu Ser Leu His Pro His Asn Asp Arg Gly Thr Gly
            275                 280                 285

Val Gly Ala Ala Glu Leu Gly Tyr Met Ala Gly Ala Asp Arg Ile Glu
        290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
                325                 330                 335

Phe Thr Asp Ile Arg Gln Ile Arg Ser Thr Val Glu Tyr Cys Asn Gln
            340                 345                 350

Leu Arg Val Pro Glu Arg His Pro Tyr Gly Gly Asp Leu Val Phe Thr
        355                 360                 365

Ala Phe Ser Gly Ser His Gln Asp Ala Val Asn Lys Gly Leu Asp Ala
    370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
                405                 410                 415

Pro Lys Asp Val Gly Arg Asp Tyr Glu Ala Val Ile Arg Val Asn Ser
            420                 425                 430

Gln Ser Gly Lys Gly Gly Val Ala Tyr Ile Met Lys Thr Asp His Gly
        435                 440                 445

Leu Gln Ile Pro Arg Ser Met Gln Val Glu Phe Ser Thr Val Val Gln
    450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
            500                 505                 510

Ile Thr Ala Glu Leu Ile His Asn Gly Lys Asp Val Thr Val Asp Gly
        515                 520                 525

His Gly Asn Gly Pro Leu Ala Ala Tyr Ala Asn Ala Leu Glu Lys Leu
    530                 535                 540

Gly Ile Asp Val Glu Ile Gln Glu Tyr Asn Gln His Ala Gln Thr Ser
545                 550                 555                 560

Asp Asp Asp Ala Glu Ala Ala Tyr Val Leu Ala Glu Val Asn Gly
                565                 570                 575

Arg Lys Val Trp Gly Val Gly Ile Ala Gly Ser Ile Thr Tyr Ala Ser
            580                 585                 590

Leu Lys Ala Val Thr Ser Ala Val Asn Arg Ala Leu Asp Val Asn His
        595                 600                 605

Glu Ala Val Leu Ala Gly Gly Val
    610                 615

<210> SEQ ID NO 34
<211> LENGTH: 616
<212> TYPE: PRT
<213> ORGANISM: Artificial Sequence
<220> FEATURE:
<223> OTHER INFORMATION: R558Q, G561R AA

<400> SEQUENCE: 34

Met Ser Pro Asn Asp Ala Phe Ile Ser Ala Pro Ala Lys Ile Glu Thr
1               5                   10                  15
```

```
Pro Val Gly Pro Arg Asn Glu Gly Gln Pro Ala Trp Asn Lys Gln Arg
             20                  25                  30

Gly Ser Ser Met Pro Val Asn Arg Tyr Met Pro Phe Glu Val Glu Val
         35                  40                  45

Glu Asp Ile Ser Leu Pro Asp Arg Thr Trp Pro Asp Lys Lys Ile Thr
 50                  55                  60

Val Ala Pro Gln Trp Cys Ala Val Asp Leu Arg Asp Gly Asn Gln Ala
 65                  70                  75                  80

Leu Ile Asp Pro Met Ser Pro Glu Arg Lys Arg Met Phe Glu Leu
                 85                  90                  95

Leu Val Gln Met Gly Phe Lys Glu Ile Glu Val Gly Phe Pro Ser Ala
             100                 105                 110

Ser Gln Thr Asp Phe Asp Phe Val Arg Glu Ile Ile Glu Lys Asp Met
         115                 120                 125

Ile Pro Asp Asp Val Thr Ile Gln Val Leu Val Gln Ala Arg Glu His
130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                 165                 170                 175

Arg Met Asp Lys Val Gln Val Lys Lys Leu Ala Thr Asp Ala Ala Glu
             180                 185                 190

Leu Ile Lys Thr Val Ala Gln Asp Tyr Pro Asp Thr Asn Trp Arg Trp
         195                 200                 205

Gln Tyr Ser Pro Glu Ser Phe Thr Gly Thr Glu Val Glu Tyr Ala Lys
210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                 245                 250                 255

Val Tyr Ala Asp Ser Ile Glu Trp Met His Arg Asn Leu Asn Arg Arg
             260                 265                 270

Asp Ser Ile Ile Leu Ser Leu His Pro His Asn Asp Arg Gly Thr Gly
         275                 280                 285

Val Gly Ala Ala Glu Leu Gly Tyr Met Ala Gly Ala Asp Arg Ile Glu
290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
                 325                 330                 335

Phe Thr Asp Ile Arg Gln Ile Arg Ser Thr Val Glu Tyr Cys Asn Gln
             340                 345                 350

Leu Arg Val Pro Glu Arg His Pro Tyr Gly Gly Asp Leu Val Phe Thr
         355                 360                 365

Ala Phe Ser Gly Ser His Gln Asp Ala Val Asn Lys Gly Leu Asp Ala
370                 375                 380

Met Ala Ala Lys Val Gln Pro Gly Ala Ser Thr Glu Val Ser Trp
385                 390                 395                 400

Glu Gln Leu Arg Asp Thr Glu Trp Glu Val Pro Tyr Leu Pro Ile Asp
                 405                 410                 415

Pro Lys Asp Val Gly Arg Asp Tyr Glu Ala Val Ile Arg Val Asn Ser
             420                 425                 430

Gln Ser Gly Lys Gly Gly Val Ala Tyr Ile Met Lys Thr Asp His Gly
```

-continued

```
                435                 440                 445
Leu Gln Ile Pro Arg Ser Met Gln Val Glu Phe Ser Thr Val Val Gln
    450                 455                 460
Asn Val Thr Asp Ala Glu Gly Gly Glu Val Asn Ser Lys Ala Met Trp
465                 470                 475                 480
Asp Ile Phe Ala Thr Glu Tyr Leu Glu Arg Thr Ala Pro Val Glu Gln
                485                 490                 495
Ile Ala Leu Arg Val Glu Asn Ala Gln Thr Glu Asn Glu Asp Ala Ser
            500                 505                 510
Ile Thr Ala Glu Leu Ile His Asn Gly Lys Asp Val Thr Val Asp Gly
        515                 520                 525
His Gly Asn Gly Pro Leu Ala Ala Tyr Ala Asn Ala Leu Glu Lys Leu
    530                 535                 540
Gly Ile Asp Val Glu Ile Gln Glu Tyr Asn Gln His Ala Gln Thr Ser
545                 550                 555                 560
Arg Asp Asp Ala Glu Ala Ala Tyr Val Leu Ala Glu Val Asn Gly
                565                 570                 575
Arg Lys Val Trp Gly Val Gly Ile Ala Gly Ser Ile Thr Tyr Ala Ser
            580                 585                 590
Leu Lys Ala Val Thr Ser Ala Val Asn Arg Ala Leu Asp Val Asn His
        595                 600                 605
Glu Ala Val Leu Ala Gly Gly Val
    610                 615

<210> SEQ ID NO 35
<211> LENGTH: 616
<212> TYPE: PRT
<213> ORGANISM: Artificial Sequence
<220> FEATURE:
<223> OTHER INFORMATION: R558Q, G561Y AA

<400> SEQUENCE: 35

Met Ser Pro Asn Asp Ala Phe Ile Ser Ala Pro Ala Lys Ile Glu Thr
1               5                   10                  15
Pro Val Gly Pro Arg Asn Glu Gly Gln Pro Ala Trp Asn Lys Gln Arg
            20                  25                  30
Gly Ser Ser Met Pro Val Asn Arg Tyr Met Pro Phe Glu Val Glu Val
        35                  40                  45
Glu Asp Ile Ser Leu Pro Asp Arg Thr Trp Pro Asp Lys Lys Ile Thr
    50                  55                  60
Val Ala Pro Gln Trp Cys Ala Val Asp Leu Arg Asp Gly Asn Gln Ala
65                  70                  75                  80
Leu Ile Asp Pro Met Ser Pro Glu Arg Lys Arg Arg Met Phe Glu Leu
                85                  90                  95
Leu Val Gln Met Gly Phe Lys Glu Ile Glu Val Gly Phe Pro Ser Ala
            100                 105                 110
Ser Gln Thr Asp Phe Asp Phe Val Arg Glu Ile Ile Glu Lys Asp Met
        115                 120                 125
Ile Pro Asp Asp Val Thr Ile Gln Val Leu Val Gln Ala Arg Glu His
    130                 135                 140
Leu Ile Arg Arg Thr Phe Glu Ala Cys Glu Gly Ala Lys Asn Val Ile
145                 150                 155                 160
Val His Phe Tyr Asn Ser Thr Ser Ile Leu Gln Arg Asn Val Val Phe
                165                 170                 175
Arg Met Asp Lys Val Gln Val Lys Lys Leu Ala Thr Asp Ala Ala Glu
```

```
                    180                 185                 190
Leu Ile Lys Thr Val Ala Gln Asp Tyr Pro Asp Thr Asn Trp Arg Trp
            195                 200                 205
Gln Tyr Ser Pro Glu Ser Phe Thr Gly Thr Glu Val Glu Tyr Ala Lys
        210                 215                 220
Glu Val Val Asp Ala Val Glu Val Met Asp Pro Thr Pro Glu Asn
225                 230                 235                 240
Pro Met Ile Ile Asn Leu Pro Ser Thr Val Glu Met Ile Thr Pro Asn
                245                 250                 255
Val Tyr Ala Asp Ser Ile Glu Trp Met His Arg Asn Leu Asn Arg Arg
            260                 265                 270
Asp Ser Ile Ile Leu Ser Leu His Pro His Asn Asp Arg Gly Thr Gly
        275                 280                 285
Val Gly Ala Ala Glu Leu Gly Tyr Met Ala Gly Ala Asp Arg Ile Glu
    290                 295                 300
Gly Cys Leu Phe Gly Asn Gly Glu Arg Thr Gly Asn Val Cys Leu Val
305                 310                 315                 320
Thr Leu Ala Leu Asn Met Leu Thr Gln Gly Val Asp Pro Gln Leu Asp
                325                 330                 335
Phe Thr Asp Ile Arg Gln Ile Arg Ser Thr Val Glu Tyr Cys Asn Gln
            340                 345                 350
Leu Arg Val Pro Glu Arg His Pro Tyr Gly Gly Asp Leu Val Phe Thr
        355                 360                 365
Ala Phe Ser Gly Ser His Gln Asp Ala Val Asn Lys Gly Leu Asp Ala
    370                 375                 380
Met Ala Ala Lys Val Gln Pro Gly Ala Ser Ser Thr Glu Val Ser Trp
385                 390                 395                 400
Glu Gln Leu Arg Asp Thr Glu Trp Glu Val Pro Tyr Leu Pro Ile Asp
                405                 410                 415
Pro Lys Asp Val Gly Arg Asp Tyr Glu Ala Val Ile Arg Val Asn Ser
            420                 425                 430
Gln Ser Gly Lys Gly Val Ala Tyr Ile Met Lys Thr Asp His Gly
        435                 440                 445
Leu Gln Ile Pro Arg Ser Met Gln Val Glu Phe Ser Thr Val Val Gln
    450                 455                 460
Asn Val Thr Asp Ala Glu Gly Gly Glu Val Asn Ser Lys Ala Met Trp
465                 470                 475                 480
Asp Ile Phe Ala Thr Glu Tyr Leu Glu Arg Thr Ala Pro Val Glu Gln
                485                 490                 495
Ile Ala Leu Arg Val Glu Asn Ala Gln Thr Glu Asn Glu Asp Ala Ser
            500                 505                 510
Ile Thr Ala Glu Leu Ile His Asn Gly Lys Asp Val Thr Val Asp Gly
        515                 520                 525
His Gly Asn Gly Pro Leu Ala Ala Tyr Ala Asn Ala Leu Glu Lys Leu
    530                 535                 540
Gly Ile Asp Val Glu Ile Gln Glu Tyr Asn Gln His Ala Gln Thr Ser
545                 550                 555                 560
Tyr Asp Asp Ala Glu Ala Ala Tyr Val Leu Ala Glu Val Asn Gly
                565                 570                 575
Arg Lys Val Trp Gly Val Gly Ile Ala Gly Ser Ile Thr Tyr Ala Ser
            580                 585                 590
Leu Lys Ala Val Thr Ser Ala Val Asn Arg Ala Leu Asp Val Asn His
        595                 600                 605
```

Glu Ala Val Leu Ala Gly Gly Val
    610             615

<210> SEQ ID NO 36
<211> LENGTH: 1851
<212> TYPE: DNA
<213> ORGANISM: Artificial Sequence
<220> FEATURE:
<223> OTHER INFORMATION: R558H NT

<400> SEQUENCE: 36

| | | | | |
|---|---|---|---|---|
| atgtctccta acgatgcatt catctccgca cctgccaaga tcgaaacccc agttgggcct | 60 |
| cgcaatgaag gccagccagc atggaataag cagcgtggct cctcaatgcc agttaaccgc | 120 |
| tacatgcctt tcgaggttga ggtagaagat atttctctgc cggaccgcac ttggccagat | 180 |
| aaaaaaatca ccgttgcacc tcagtggtgt gctgttgacc tgcgtgacgg caaccaggct | 240 |
| ctgattgatc cgatgtctcc tgagcgtaag cgccgcatgt ttgagctgct ggttcagatg | 300 |
| ggattcaagg aaatcgaggt cggtttccct tcagcttccc agactgattt tgatttcgtt | 360 |
| cgtgagatca tcgaaaagga catgatccct gacgatgtca ccattcaggt tctggttcag | 420 |
| gctcgtgagc acctgattcg ccgtactttt gaagcttgcg aaggcgcaaa aaacgttatc | 480 |
| gtgcacttct acaactcaac ctccatcctg cagcgcaacg tggtgttccg catggacaag | 540 |
| gtgcaggtga agaagctggc taccgatgcc gctgaactga tcaagaccgt cgctcaggat | 600 |
| tacccagaca ccaactggcg ctggcagtac tcccctgagt ccttcaccgg cactgaggtt | 660 |
| gagtacgcca aggaagttgt ggacgcagtt gttgaggtca tggatccaac tcctgagaac | 720 |
| ccaatgatca tcaacctgcc ttccaccgtt gagatgatca cccctaacgt ttacgcagac | 780 |
| tccattgaat ggatgcaccg caatctaaac cgtcgtgatt ccattatcct gtccctgcac | 840 |
| ccgcacaatg accgtggcac cggcgttggc gcagctgagc tgggctacat ggctggcgct | 900 |
| gaccgcatcg aaggctgcct gttcggcaac ggcgagcgca ccggcaacgt ctgcctggtc | 960 |
| accctggcac tgaacatgct gacccagggc gttgaccctc agctggactt caccgatata | 1020 |
| cgccagatcc gcagcaccgt tgaatactgc aaccagctgc gcgttcctga gcgccaccca | 1080 |
| tacggcggcg acctggtctt caccgctttc tccggttccc accaggacgc tgtgaacaag | 1140 |
| ggtctggacg ccatggctgc caaggttcag ccaggtgcta gctccactga gtttcttgg | 1200 |
| gagcagctgc gcgacaccga tgggaggtt ccttacctgc ctatcgatcc aaaggatgtc | 1260 |
| ggtcgcgact acgaggctgt tatccgcgtg aactcccagt ccggcaaggg cggcgttgct | 1320 |
| tacatcatga gaccgatca cggtctgcag atccctcgct ccatgcaggt tgagttctcc | 1380 |
| accgttgtcc agaacgtcac cgacgctgag ggcggcgagg tcaactccaa ggcaatgtgg | 1440 |
| gatatcttcg ccaccgagta cctggagcgc accgcaccag ttgagcagat cgcgctgcgc | 1500 |
| gtcgagaacg ctcagaccga aaacgaggat gcatccatca ccgccgagct catccacaac | 1560 |
| ggcaaggacg tcaccgtcga tgccacggc aacggcccac tggctgctta cgccaacgcg | 1620 |
| ctggagaagc tgggcatcga cgttgagatc caggaataca accagcacgc ccacacctcg | 1680 |
| ggcgacgatg cagaagcagc cgcctacgtg ctggctgagg tcaacggccg caaggtctgg | 1740 |
| ggcgtcggca tcgctggctc catcacctac gcttcgctga aggcagtgac ctccgccgta | 1800 |
| aaccgcgcgc tggacgtcaa ccacgaggca gtcctggctg cggcgtttta a | 1851 |

<210> SEQ ID NO 37
<211> LENGTH: 1851

<212> TYPE: DNA
<213> ORGANISM: Artificial Sequence
<220> FEATURE:
<223> OTHER INFORMATION: R558A NT

<400> SEQUENCE: 37

```
atgtctccta acgatgcatt catctccgca cctgccaaga tcgaaacccc agttgggcct      60
cgcaatgaag gccagccagc atggaataag cagcgtggct cctcaatgcc agttaaccgc     120
tacatgcctt tcgaggttga ggtagaagat atttctctgc cggaccgcac ttggccagat     180
aaaaaaatca ccgttgcacc tcagtggtgt gctgttgacc tgcgtgacgg caaccaggct     240
ctgattgatc cgatgtctcc tgagcgtaag cgccgcatgt tgagctgct  ggttcagatg     300
ggattcaagg aaatcgaggt cggtttccct tcagcttccc agactgattt tgatttcgtt     360
cgtgagatca tcgaaaagga catgatccct gacgatgtca ccattcaggt tctggttcag     420
gctcgtgagc acctgattcg ccgtactttt gaagcttgcg aaggcgcaaa aaacgttatc     480
gtgcacttct acaactcaac ctccatcctg cagcgcaacg tggtgttccg catggacaag     540
gtgcaggtga agaagctggc taccgatgcc gctgaactga tcaagaccgt cgctcaggat     600
tacccagaca ccaactggcg ctggcagtac tcccctgagt ccttcaccgg cactgaggtt     660
gagtacgcca aggaagttgt ggacgcagtt gttgaggtca tggatccaac tcctgagaac     720
ccaatgatca tcaacctgcc ttccaccgtt gagatgatca ccctaacgt  ttacgcagac     780
tccattgaat ggatgcaccg caatctaaac cgtcgtgatt ccattatcct gtccctgcac     840
ccgcacaatg accgtggcac cggcgttggc gcagctgagc tgggctacat ggctggcgct     900
gaccgcatcg aaggctgcct gttcggcaac ggcgagcgca ccggcaacgt ctgcctggtc     960
accctggcac tgaacatgct gacccagggc gttgaccctc agctggactt caccgatata    1020
cgccagatcc gcagcaccgt tgaatactgc aaccagctgc gcgttcctga gcgccaccca    1080
tacggcggcg acctggtctt caccgctttc tccggttccc accaggacgc tgtgaacaag    1140
ggtctggacg ccatggctgc caaggttcag ccaggtgcta gctccactga gtttcttgg     1200
gagcagctgc gcgacaccga atgggaggtt ccttacctgc ctatcgatcc aaaggatgtc    1260
ggtcgcgact acgaggctgt tatccgcgtg aactcccagt ccggcaaggg cggcgttgct    1320
tacatcatga agaccgatca cggtctgcag atccctcgct ccatgcaggt tgagttctcc    1380
accgttgtcc agaacgtcac cgacgctgag ggcggcgagg tcaactccaa ggcaatgtgg    1440
gatatcttcg ccaccgagta cctggagcgc accgcaccag ttgagcagat cgcgctgcgc    1500
gtcgagaacc tcagaccga  aaacgaggat gcatccatca ccgccgagct catccacaac    1560
ggcaaggacg tcaccgtcga tggccacggc aacggcccac tggctgctta cgccaacgcg    1620
ctggagaagc tgggcatcga cgttgagatc caggaataca accagcacgc cgcaacctcg    1680
ggcgacgatg cagaagcagc cgcctacgtg ctggctgagg tcaacggccg caaggtctgg    1740
ggcgtcggca tcgctggctc catcacctac gcttcgctga aggcagtgac ctccgccgta    1800
aaccgcgcgc tggacgtcaa ccacgaggca gtcctggctg gcggcgttta a             1851
```

<210> SEQ ID NO 38
<211> LENGTH: 1851
<212> TYPE: DNA
<213> ORGANISM: Artificial Sequence
<220> FEATURE:
<223> OTHER INFORMATION: R558Q NT

<400> SEQUENCE: 38

```
atgtctccta acgatgcatt catctccgca cctgccaaga tcgaaacccc agttgggcct      60
cgcaatgaag gccagccagc atggaataag cagcgtggct cctcaatgcc agttaaccgc     120
tacatgcctt tcgaggttga ggtagaagat atttctctgc cggaccgcac ttggccagat     180
aaaaaaatca ccgttgcacc tcagtggtgt gctgttgacc tgcgtgacgg caaccaggct     240
ctgattgatc cgatgtctcc tgagcgtaag cgccgcatgt ttgagctgct ggttcagatg     300
ggattcaagg aaatcgaggt cggtttccct tcagcttccc agactgattt tgatttcgtt     360
cgtgagatca tcgaaaagga catgatccct gacgatgtca ccattcaggt tctggttcag     420
gctcgtgagc acctgattcg ccgtactttt gaagcttgcg aaggcgcaaa aaacgttatc     480
gtgcacttct acaactcaac ctccatcctg cagcgcaacg tggtgttccg catggacaag     540
gtgcaggtga agaagctggc taccgatgcc gctgaactga tcaagaccgt cgctcaggat     600
tacccagaca ccaactggcg ctggcagtac tcccctgagt ccttcaccgg cactgaggtt     660
gagtacgcca aggaagttgt ggacgcagtt gttgaggtca tggatccaac tcctgagaac     720
ccaatgatca tcaacctgcc ttccaccgtt gagatgatca cccctaacgt ttacgcagac     780
tccattgaat ggatgcaccg caatctaaac cgtcgtgatt ccattatcct gtccctgcac     840
ccgcacaatg accgtggcac cggcgttggc gcagctgagc tgggctacat ggctggcgct     900
gaccgcatcg aaggctgcct gttcggcaac ggcgagcgca ccggcaacgt ctgcctggtc     960
accctggcac tgaacatgct gacccagggc gttgaccctc agctggactt caccgatata    1020
cgccagatcc gcagcaccgt tgaatactgc aaccagctgc gcgttcctga gcgccaccca    1080
tacggcggcg aacctggtct tcaccgcttt c tccggttccc accaggacgc tgtgaacaag    1140
ggtctggacg ccatggctgc caaggttcag ccaggtgcta gctccactga gtttcttgg    1200 gagcagctgc gcgacaccga atgggaggtt ccttacctgc ctatcgatcc aaaggatgtc    1260
ggtcgcgact acgaggctgt tatccgcgtg aactcccagt ccggcaaggg cggcgttgct    1320
tacatcatga gaccgatca cggtctgcag atccctcgct ccatgcaggt tgagttctcc    1380
accgttgtcc agaacgtcac cgacgctgag ggcggcgagg tcaactccaa ggcaatgtgg    1440
gatatcttcg ccaccgagta cctggagcgc accgcaccag ttgagcagat cgcgctgcgc    1500
gtcgagaacg ctcagaccga aaacgaggat gcatccatca ccgccgagct catccacaac    1560
ggcaaggacg tcaccgtcga tggccacggc aacggcccac tggctgctta cgccaacgcg    1620
ctggagaagc tgggcatcga cgttgagatc caggaataca accagcacgc ccagacctcg    1680
ggcgacgatg cagaagcagc cgcctacgtg ctggctgagg tcaacggccg caaggtctgg    1740
ggcgtcggca tcgctggctc catcacctac gcttcgctga aggcagtgac ctccgccgta    1800
aaccgcgcgc tggacgtcaa ccacgaggca gtcctggctg gcggcgttta a            1851
```

<210> SEQ ID NO 39
<211> LENGTH: 1851
<212> TYPE: DNA
<213> ORGANISM: Artificial Sequence
<220> FEATURE:
<223> OTHER INFORMATION: G561D NT

<400> SEQUENCE: 39

```
atgtctccta acgatgcatt catctccgca cctgccaaga tcgaaacccc agttgggcct      60
cgcaatgaag gccagccagc atggaataag cagcgtggct cctcaatgcc agttaaccgc     120
tacatgcctt tcgaggttga ggtagaagat atttctctgc cggaccgcac ttggccagat     180
aaaaaaatca ccgttgcacc tcagtggtgt gctgttgacc tgcgtgacgg caaccaggct     240
```

```
ctgattgatc cgatgtctcc tgagcgtaag cgccgcatgt ttgagctgct ggttcagatg      300
ggattcaagg aaatcgaggt cggtttccct tcagcttccc agactgattt tgatttcgtt      360
cgtgagatca tcgaaaagga catgatccct gacgatgtca ccattcaggt tctggttcag      420
gctcgtgagc acctgattcg ccgtactttt gaagcttgcg aaggcgcaaa aaacgttatc      480
gtgcacttct acaactcaac ctccatcctg cagcgcaacg tggtgttccg catggacaag      540
gtgcaggtga gaagctggc taccgatgcc gctgaactga tcaagaccgt cgctcaggat       600
tacccagaca ccaactggcg ctggcagtac tcccctgagt ccttcaccgg cactgaggtt      660
gagtacgcca aggaagttgt ggacgcagtt gttgaggtca tggatccaac tcctgagaac      720
ccaatgatca tcaacctgcc ttccaccgtt gagatgatca cccctaacgt ttacgcagac      780
tccattgaat ggatgcaccg caatctaaac cgtcgtgatt ccattatcct gtccctgcac      840
ccgcacaatg accgtggcac cggcgttggc gcagctgagc tgggctacat ggctggcgct      900
gaccgcatcg aaggctgcct gttcggcaac ggcgagcgca ccggcaacgt ctgcctggtc      960
accctggcac tgaacatgct gacccagggc gttgacccct cagctggactt caccgatata   1020 cgccagatcc gcagcaccgt tgaatactgc aaccagctgc gcgttcctga gcgccaccca     1080
tacggcggcg acctggtctt caccgctttc tccggttccc accaggacgc tgtgaacaag     1140
ggtctggacg ccatggctgc caaggttcag ccaggtgcta gctccactga gtttcttgg      1200 gagcagctgc gcgacaccga atgggaggtt ccttacctgc ctatcgatcc aaaggatgtc     1260
ggtcgcgact acgaggctgt tatccgcgtg aactcccagt ccggcaaggg cggcgttgct     1320
tacatcatga agaccgatca cggtctgcag atccctcgct ccatgcaggt tgagttctcc     1380
accgttgtcc agaacgtcac cgacgctgag ggcggcgagg tcaactccaa ggcaatgtgg     1440
gatatcttcg ccaccgagta cctggagcgc accgcaccag ttgagcagat cgcgctgcgc     1500
gtcgagaacg ctcagaccga aaacgaggat gcatccatca ccgccgagct catccacaac     1560
ggcaaggacg tcaccgtcga tggccacggc aacgccccac tggctgctta cgccaacgcg     1620
ctggagaagc tgggcatcga cgttgagatc caggaataca accagcacgc ccgcacctcg     1680
gatgacgatg cagaagcagc cgcctacgtg ctggctgagg tcaacggccg caaggtctgg     1740
ggcgtcggca tcgctggctc catcacctac gcttcgctga aggcagtgac ctccgccgta     1800
aaccgcgcgc tggacgtcaa ccacgaggca gtcctggctg cggcgtttta a              1851
```

<210> SEQ ID NO 40
<211> LENGTH: 1851
<212> TYPE: DNA
<213> ORGANISM: Artificial Sequence
<220> FEATURE:
<223> OTHER INFORMATION: G561R NT

<400> SEQUENCE: 40

```
atgtctccta cgatgcatt catctccgca cctgccaaga tcgaaccccc agttgggcct        60
cgcaatgaag gccagccagc atggaataag cagcgtggct cctcaatgcc agttaaccgc      120
tacatgcctt tcgaggttga ggtagaagat atttctctgc cggaccgcac ttggccagat      180
aaaaaaatca ccgttgcacc tcagtggtgt gctgttgacc tgcgtgacgg caaccaggct      240
ctgattgatc cgatgtctcc tgagcgtaag cgccgcatgt ttgagctgct ggttcagatg      300
ggattcaagg aaatcgaggt cggtttccct tcagcttccc agactgattt tgatttcgtt      360
cgtgagatca tcgaaaagga catgatccct gacgatgtca ccattcaggt tctggttcag      420
```

```
gctcgtgagc acctgattcg ccgtactttt gaagcttgcg aaggcgcaaa aaacgttatc    480
gtgcacttct acaactcaac ctccatcctg cagcgcaacg tggtgttccg catggacaag    540
gtgcaggtga agaagctggc taccgatgcc gctgaactga tcaagaccgt cgctcaggat    600
tacccagaca ccaactggcg ctggcagtac tcccctgagt ccttcaccgg cactgaggtt    660
gagtacgcca aggaagttgt ggacgcagtt gttgaggtca tggatccaac tcctgagaac    720
ccaatgatca tcaacctgcc ttccaccgtt gagatgatca cccctaacgt ttacgcagac    780
tccattgaat ggatgcaccg caatctaaac cgtcgtgatt ccattatcct gtccctgcac    840
ccgcacaatg accgtggcac cggcgttggc gcagctgagc tgggctacat ggctggcgct    900
gaccgcatcg aaggctgcct gttcggcaac ggcgagcgca ccggcaacgt ctgcctggtc    960
accctggcac tgaacatgct gacccagggc gttgaccctc agctggactt caccgatata   1020
cgccagatcc gcagcaccgt tgaatactgc aaccagctgc gcgttcctga gcgccaccca   1080
tacggcggcg acctggtctt caccgctttc tccggttccc accaggacgc tgtgaacaag   1140
ggtctggacg ccatggctgc caaggttcag ccaggtgcta gctccactga gtttcttgg    1200
gagcagctgc gcgacaccga atgggaggtt ccttacctgc ctatcgatcc aaaggatgtc   1260
ggtcgcgact acgaggctgt tatccgcgtg aactcccagt ccggcaaggg cggcgttgct   1320
tacatcatga gaccgatca cggtctgcag atccctcgct ccatgcaggt tgagttctcc   1380
accgttgtcc agaacgtcac cgacgctgag ggcggcgagg tcaactccaa ggcaatgtgg   1440
gatatcttcg ccaccgagta cctggagcgc accgcaccag ttgagcagat cgcgctgcgc   1500
gtcgagaacc tcagaccga aaacgaggat gcatccatca ccgccgagct catccacaac   1560
ggcaaggacg tcaccgtcga tggccacggc aacggcccac tggctgctta cgccaacgcg   1620
ctggagaagc tgggcatcga cgttgagatc caggaataca accagcacgc ccgcacctcg   1680
cgcgacgatg cagaagcagc cgcctacgtg ctggctgagg tcaacggccg caaggtctgg   1740
ggcgtcggca tcgctggctc catcacctac gcttcgctga aggcagtgac ctccgccgta   1800
aaccgcgcgc tggacgtcaa ccacgaggca gtcctggctg gcggcgttta a            1851
```

<210> SEQ ID NO 41
<211> LENGTH: 1851
<212> TYPE: DNA
<213> ORGANISM: Artificial Sequence
<220> FEATURE:
<223> OTHER INFORMATION: G561Y NT

<400> SEQUENCE: 41

```
atgtctccta cgatgcatt catctccgca cctgccaaga tcgaaacccc agttgggcct     60
cgcaatgaag gccagccagc atggaataag cagcgtggct cctcaatgcc agttaaccgc    120
tacatgcctt tcgaggttga ggtagaagat atttctctgc cggaccgcac ttggccagat    180
aaaaaaatca ccgttgcacc tcagtggtgt gctgttgacc tcgtgacgg caaccaggct    240
ctgattgatc cgatgtctcc tgagcgtaag cgccgcatgt tgagctgct ggttcagatg    300
ggattcaagg aaatcgaggt cggtttccct tcagcttccc agactgattt tgatttcgtt    360
cgtgagatca tcgaaaagga catgatccct gacgatgtca ccattcaggt tctggttcag    420
gctcgtgagc acctgattcg ccgtactttt gaagcttgcg aaggcgcaaa aaacgttatc    480
gtgcacttct acaactcaac ctccatcctg cagcgcaacg tggtgttccg catggacaag    540
gtgcaggtga agaagctggc taccgatgcc gctgaactga tcaagaccgt cgctcaggat    600
tacccagaca ccaactggcg ctggcagtac tcccctgagt ccttcaccgg cactgaggtt    660
```

```
gagtacgcca aggaagttgt ggacgcagtt gttgaggtca tggatccaac tcctgagaac    720
ccaatgatca tcaacctgcc ttccaccgtt gagatgatca cccctaacgt ttacgcagac    780
tccattgaat ggatgcaccg caatctaaac cgtcgtgatt ccattatcct gtccctgcac    840
ccgcacaatg accgtggcac cggcgttggc gcagctgagc tgggctacat ggctggcgct    900
gaccgcatcg aaggctgcct gttcggcaac ggcgagcgca ccggcaacgt ctgcctggtc    960
accctggcac tgaacatgct gacccagggc gttgaccctc agctggactt caccgatata   1020
cgccagatcc gcagcaccgt tgaatactgc aaccagctgc gcgttcctga gcgccaccca   1080
tacggcggcg acctggtctt caccgctttc tccggttccc accaggacgc tgtgaacaag   1140
ggtctggacg ccatggctgc caaggttcag ccaggtgcta gctccactga gtttcttgg    1200 gagcagctgc gcgacaccga atgggaggtt ccttacctgc ctatcgatcc aaaggatgtc   1260
ggtcgcgact acgaggctgt tatccgcgtg aactcccagt ccggcaaggg cggcgttgct   1320
tacatcatga gaccgatca cggtctgcag atccctcgct ccatgcaggt tgagttctcc   1380
accgttgtcc agaacgtcac cgacgctgag ggcggcgagg tcaactccaa ggcaatgtgg   1440
gatatcttcg ccaccgagta cctggagcgc accgcaccag ttgagcagat cgcgctgcgc   1500
gtcgagaacg ctcagaccga aaacgaggat gcatccatca ccgccgagct catccacaac   1560
ggcaaggacg tcaccgtcga tggccacggc aacggcccac tggctgctta cgccaacgcg   1620
ctggagaagc tgggcatcga cgttgagatc caggaataca accagcacgc ccgcacctcg   1680
tacgacgatg cagaagcagc cgcctacgtg ctggctgagg tcaacggccg caaggtctgg   1740
ggcgtcggca tcgctggctc catcacctac gcttcgctga aggcagtgac ctccgccgta   1800
aaccgcgcgc tggacgtcaa ccacgaggca gtcctggctg gcggcgttta a           1851

<210> SEQ ID NO 42
<211> LENGTH: 1851
<212> TYPE: DNA
<213> ORGANISM: Artificial Sequence
<220> FEATURE:
<223> OTHER INFORMATION: R558H, G561D NT

<400> SEQUENCE: 42
atgtctccta acgatgcatt catctccgca cctgccaaga tcgaaacccc agttgggcct     60
cgcaatgaag ccagccagc atggaataag cagcgtggct cctcaatgcc agttaaccgc    120
tacatgcctt tcgaggttga ggtagaagat atttctctgc cggaccgcac ttggccagat    180
aaaaaaatca ccgttgcacc tcagtggtgt gctgttgacc tgcgtgacgg caaccaggct    240
ctgattgatc cgatgtctcc tgagcgtaag cgccgcatgt ttgagctgct ggttcagatg    300
ggattcaagg aaatcgaggt cggtttccct tcagcttccc agactgattt tgatttcgtt    360
cgtgagatca tcgaaaagga catgatccct gacgatgtca ccattcaggt tctggttcag    420
gctcgtgagc acctgattcg ccgtacttt gaagcttgcg aaggcgcaaa aaacgttatc    480
gtgcacttct acaactcaac ctccatcctg cagcgcaacg tggtgttccg catggacaag    540
gtgcaggtga agaagctggc taccgatgcc gctgaactga tcaagaccgt cgctcaggat    600
tacccagaca ccaactggcg ctggcagtac tcccctgagt ccttcaccgg cactgaggtt    660
gagtacgcca aggaagttgt ggacgcagtt gttgaggtca tggatccaac tcctgagaac    720
ccaatgatca tcaacctgcc ttccaccgtt gagatgatca cccctaacgt ttacgcagac    780
tccattgaat ggatgcaccg caatctaaac cgtcgtgatt ccattatcct gtccctgcac    840
```

```
ccgcacaatg accgtggcac cggcgttggc gcagctgagc tgggctacat ggctggcgct    900
gaccgcatcg aaggctgcct gttcggcaac ggcgagcgca ccggcaacgt ctgcctggtc    960
accctggcac tgaacatgct gacccagggc gttgaccctc agctggactt caccgatata   1020
cgccagatcc gcagcaccgt tgaatactgc aaccagctgc gcgttcctga cgccacccca   1080
tacggcggcg acctggtctt caccgctttc tccggttccc accaggacgc tgtgaacaag   1140
ggtctggacg ccatggctgc caaggttcag ccaggtgcta gctccactga gtttcttgg    1200
gagcagctgc gcgacaccga atgggaggtt ccttacctgc ctatcgatcc aaaggatgtc   1260
ggtcgcgact acgaggctgt tatccgcgtg aactcccagt ccggcaaggg cggcgttgct   1320
tacatcatga agaccgatca cggtctgcag atccctcgct ccatgcaggt tgagttctcc   1380
accgttgtcc agaacgtcac cgacgctgag ggcggcgagg tcaactccaa ggcaatgtgg   1440
gatatcttcg ccaccgagta cctggagcgc accgcaccag ttgagcagat cgcgctgcgc   1500
gtcgagaacg ctcagaccga aaacgaggat gcatccatca ccgccgagct catccacaac   1560
ggcaaggacg tcaccgtcga tgccacggc aacgccccca tggctgctta cgccaacgcg    1620
ctggagaagc tgggcatcga cgttgagatc caggaataca accagcacgc ccacacctcg   1680
gatgacgatg cagaagcagc cgcctacgtg ctggctgagg tcaacggccg caaggtctgg   1740
ggcgtcggca tcgctggctc catcacctac gcttcgctga aggcagtgac ctccgccgta   1800
aaccgcgcgc tggacgtcaa ccacgaggca gtcctggctg gcggcgttta a            1851

<210> SEQ ID NO 43
<211> LENGTH: 1851
<212> TYPE: DNA
<213> ORGANISM: Artificial Sequence
<220> FEATURE:
<223> OTHER INFORMATION: R558H, G561R NT

<400> SEQUENCE: 43
atgtctccta cgatgcatt catctccgca cctgccaaga tcgaaacccc agttgggcct      60
cgcaatgaag gccagccagc atggaataag cagcgtggct cctcaatgcc agttaaccgc    120
tacatgcctt tcgaggttga ggtagaagat atttctctgc cggaccgcac ttggccagat    180
aaaaaaatca ccgttgcacc tcagtggtgt gctgttgacc tgcgtgacgg caaccaggct    240
ctgattgatc cgatgtctcc tgagcgtaag cgccgcatgt ttgagctgct ggttcagatg    300
ggattcaagg aaatcgaggt cggtttccct tcagcttccc agactgattt tgatttcgtt    360
cgtgagatca tcgaaaagga catgatccct gacgatgtca ccattcaggt tctggttcag    420
gctcgtgagc acctgattcg ccgtactttt gaagcttgcg aaggcgcaaa aaacgttatc    480
gtgcacttct acaactcaac ctccatcctg cagcgcaacg tggtgttccg catggacaag    540
gtgcaggtga agaagctggc taccgatgcc gctgaactga tcaagaccgt cgctcaggat    600
tacccagaca ccaactggcg ctggcagtac tcccctgagt ccttcaccgg cactgaggtt    660
gagtacgcca aggaagttgt ggacgcagtt gttgaggtca tggatccaac tcctgagaac    720
ccaatgatca tcaacctgcc ttccaccgtt gagatgatca cccctaacgt ttacgcagac    780
tccattgaat ggatgcaccg caatctaaac cgtcgtgatt ccattatcct gtccctgcac    840
ccgcacaatg accgtggcac cggcgttggc gcagctgagc tgggctacat ggctggcgct    900
gaccgcatcg aaggctgcct gttcggcaac ggcgagcgca ccggcaacgt ctgcctggtc    960
accctggcac tgaacatgct gacccagggc gttgaccctc agctggactt caccgatata   1020
cgccagatcc gcagcaccgt tgaatactgc aaccagctgc gcgttcctga cgccacccca   1080
```

```
tacggcggcg acctggtctt caccgctttc tccggttccc accaggacgc tgtgaacaag    1140
ggtctggacg ccatggctgc caaggttcag ccaggtgcta gctccactga agtttcttgg    1200
gagcagctgc gcgacaccga atgggaggtt ccttacctgc ctatcgatcc aaaggatgtc    1260
ggtcgcgact acgaggctgt tatccgcgtg aactcccagt ccggcaaggg cggcgttgct    1320
tacatcatga agaccgatca cggtctgcag atccctcgct ccatgcaggt tgagttctcc    1380
accgttgtcc agaacgtcac cgacgctgag ggcggcgagg tcaactccaa ggcaatgtgg    1440
gatatcttcg ccaccgagta cctggagcgc accgcaccag ttgagcagat cgcgctgcgc    1500
gtcgagaacg ctcagaccga aaacgaggat gcatccatca ccgccgagct catccacaac    1560
ggcaaggacg tcaccgtcga tggccacggc aacggcccac tggctgctta cgccaacgcg    1620
ctggagaagc tgggcatcga cgttgagatc caggaataca accagcacgc ccacacctcg    1680
cgcgacgatg cagaagcagc cgcctacgtg ctggctgagg tcaacggccg caaggtctgg    1740
ggcgtcggca tcgctggctc catcacctac gcttcgctga aggcagtgac ctccgccgta    1800
aaccgcgcgc tggacgtcaa ccacgaggca gtcctggctg gcggcgttta a             1851

<210> SEQ ID NO 44
<211> LENGTH: 1851
<212> TYPE: DNA
<213> ORGANISM: Artificial Sequence
<220> FEATURE:
<223> OTHER INFORMATION: R558H, G561Y NT

<400> SEQUENCE: 44
atgtctccta acgatgcatt catctccgca cctgccaaga tcgaaacccc agttgggcct      60
cgcaatgaag gccagccagc atggaataag cagcgtggct cctcaatgcc agttaaccgc     120
tacatgcctt tcgaggttga ggtagaagat atttctctgc cggaccgcac ttggccagat     180
aaaaaaatca ccgttgcacc tcagtggtgt gctgttgacc tgcgtgacgg caaccaggct     240
ctgattgatc cgatgtctcc tgagcgtaag cgccgcatgt tgagctgct ggttcagatg     300 ggattcaagg aaatcgaggt cggtttccct tcagcttccc agactgattt tgatttcgtt     360
cgtgagatca tcgaaaagga catgatccct gacgatgtca ccattcaggt tctggttcag     420
gctcgtgagc acctgattcg ccgtactttt gaagcttgcg aaggcgcaaa aacgttatc     480 gtgcacttct acaactcaac ctccatcctg agcgcaacg tggtgttccg catggacaag     540
gtgcaggtga agaagctggc taccgatgcc gctgaactga tcaagaccgt cgctcaggat     600
tacccagaca ccaactggcg ctggcagtac tcccctgagt ccttcaccgg cactgaggtt     660
gagtacgcca aggaagttgt ggacgcagtt gttgaggtca tggatccaac tcctgagaac     720
ccaatgatca tcaacctgcc ttccaccgtt gagatgatca cccctaacgt ttacgcagac     780
tccattgaat ggatgcaccg caatctaaac cgtcgtgatt ccattatcct gtccctgcac     840
ccgcacaatg accgtggcac cggcgttggc gcagctgagc tgggctacat ggctggcgct     900
gaccgcatcg aaggctgcct gttcggcaac ggcgagcgca ccggcaacgt ctgcctggtc     960
accctggcac tgaacatgct gacccagggc gttgaccctc agctggactt caccgatata    1020
cgccagatcc gcagcaccgt tgaatactgc aaccagctgc gcgttcctga cgccacccca    1080
tacggcggcg acctggtctt caccgctttc tccggttccc accaggacgc tgtgaacaag    1140
ggtctggacg ccatggctgc caaggttcag ccaggtgcta gctccactga agtttcttgg    1200
gagcagctgc gcgacaccga atgggaggtt ccttacctgc ctatcgatcc aaaggatgtc    1260
```

| | |
|---|---|
| ggtcgcgact acgaggctgt tatccgcgtg aactcccagt ccggcaaggg cggcgttgct | 1320 |
| tacatcatga agaccgatca cggtctgcag atccctcgct ccatgcaggt tgagttctcc | 1380 |
| accgttgtcc agaacgtcac cgacgctgag ggcggcgagg tcaactccaa ggcaatgtgg | 1440 |
| gatatcttcg ccaccgagta cctggagcgc accgcaccag ttgagcagat cgcgctgcgc | 1500 |
| gtcgagaacg ctcagaccga aaacgaggat gcatccatca ccgccgagct catccacaac | 1560 |
| ggcaaggact caccgtcga tggccacggc aacggcccac tggctgctta cgccaacgcg | 1620 |
| ctggagaagc tgggcatcga cgttgagatc caggaataca accagcacgc ccacacctcg | 1680 |
| tacgacgatg cagaagcagc cgcctacgtg ctggctgagg tcaacggccg caaggtctgg | 1740 |
| ggcgtcggca tcgctggctc catcacctac gcttcgctga aggcagtgac ctccgccgta | 1800 |
| aaccgcgcgc tggacgtcaa ccacgaggca gtcctggctg cggcgtttta a | 1851 |

<210> SEQ ID NO 45
<211> LENGTH: 1851
<212> TYPE: DNA
<213> ORGANISM: Artificial Sequence
<220> FEATURE:
<223> OTHER INFORMATION: R558A, G561D NT

<400> SEQUENCE: 45

| | |
|---|---|
| atgtctccta cgatgcatt catctccgca cctgccaaga tcgaaacccc agttgggcct | 60 |
| cgcaatgaag gccagccagc atggaataag cagcgtggct cctcaatgcc agttaaccgc | 120 |
| tacatgcctt cgaggttga ggtagaagat atttctctgc cggaccgcac ttggccagat | 180 |
| aaaaaaatca ccgttgcacc tcagtggtgt gctgttgacc tgcgtgacgg caaccaggct | 240 |
| ctgattgatc cgatgtctcc tgagcgtaag cgccgcatgt ttgagctgct ggttcagatg | 300 |
| ggattcaagg aaatcgaggt cggtttccct tcagcttccc agactgattt tgatttcgtt | 360 |
| cgtgagatca tcgaaaagga catgatccct gacgatgtca ccattcaggt tctggttcag | 420 |
| gctcgtgagc acctgattcg ccgtactttt gaagcttgcg aaggcgcaaa aaacgttatc | 480 |
| gtgcacttct acaactcaac ctccatcctg cagcgcaacg tggtgttccg catggacaag | 540 |
| gtgcaggtga agaagctggc taccgatgcc gctgaactga tcaagaccgt cgctcaggat | 600 |
| tacccagaca ccaactggcg ctggcagtac tcccctgagt ccttcaccgg cactgaggtt | 660 |
| gagtacgcca aggaagttgt ggacgcagtt gttgaggtca tggatccaac tcctgagaac | 720 |
| ccaatgatca tcaacctgcc ttccaccgtt gagatgatca cccctaacgt ttacgcagac | 780 |
| tccattgaat ggatgcaccg caatctaaac cgtcgtgatt ccattatcct gtccctgcac | 840 |
| ccgcacaatg accgtggcac cggcgttggc gcagctgagc tgggctacat ggctggcgct | 900 |
| gaccgcatcg aaggctgcct gttcggcaac ggcgagcgca ccggcaacgt ctgcctggtc | 960 |
| accctggcac tgaacatgct gacccagggc gttgaccctc agctggactt caccgatata | 1020 |
| cgccagatcc gcagcaccgt tgaatactgc aaccagctgc gcgttcctga gcgccaccca | 1080 |
| tacggcggcg acctggtctt caccgctttc tccggttccc accaggacgc tgtgaacaag | 1140 |
| ggtctggacg ccatggctgc caaggttcag ccaggtgcta gctccactga gtttcttgg | 1200 |
| gagcagctgc gcgacaccga atgggaggtt ccttacctgc ctatcgatcc aaaggatgtc | 1260 |
| ggtcgcgact acgaggctgt tatccgcgtg aactcccagt ccggcaaggg cggcgttgct | 1320 |
| tacatcatga agaccgatca cggtctgcag atccctcgct ccatgcaggt tgagttctcc | 1380 |
| accgttgtcc agaacgtcac cgacgctgag ggcggcgagg tcaactccaa ggcaatgtgg | 1440 |
| gatatcttcg ccaccgagta cctggagcgc accgcaccag ttgagcagat cgcgctgcgc | 1500 |

| | |
|---|---|
| gtcgagaacg ctcagaccga aaacgaggat gcatccatca ccgccgagct catccacaac | 1560 |
| ggcaaggacg tcaccgtcga tggccacggc aacggcccac tggctgctta cgccaacgcg | 1620 |
| ctggagaagc tgggcatcga cgttgagatc caggaataca accagcacgc cgcaacctcg | 1680 |
| gatgacgatg cagaagcagc cgcctacgtg ctggctgagg tcaacggccg caaggtctgg | 1740 |
| ggcgtcggca tcgctggctc catcacctac gcttcgctga aggcagtgac ctccgccgta | 1800 |
| aaccgcgcgc tggacgtcaa ccacgaggca gtcctggctg gcggcgttta a | 1851 |

<210> SEQ ID NO 46
<211> LENGTH: 1851
<212> TYPE: DNA
<213> ORGANISM: Artificial Sequence
<220> FEATURE:
<223> OTHER INFORMATION: R558A, G561R NT

<400> SEQUENCE: 46

| | |
|---|---|
| atgtctccta cgatgcatt catctccgca cctgccaaga tcgaaacccc agttgggcct | 60 |
| cgcaatgaag gccagccagc atggaataag cagcgtggct cctcaatgcc agttaaccgc | 120 |
| tacatgcctt tcgaggttga ggtagaagat atttctctgc cggaccgcac ttggccagat | 180 |
| aaaaaaatca ccgttgcacc tcagtggtgt gctgttgacc tgcgtgacgg caaccaggct | 240 |
| ctgattgatc cgatgtctcc tgagcgtaag cgccgcatgt ttgagctgct ggttcagatg | 300 |
| ggattcaagg aaatcgaggt cggtttccct tcagcttccc agactgattt tgatttcgtt | 360 |
| cgtgagatca tcgaaaagga catgatccct gacgatgtca ccattcaggt tctggttcag | 420 |
| gctcgtgagc acctgattcg ccgtactttt gaagcttgcg aaggcgcaaa aaacgttatc | 480 |
| gtgcacttct acaactcaac ctccatcctg cagcgcaacg tggtgttccg catggacaag | 540 |
| gtgcaggtga agaagctggc taccgatgcc gctgaactga tcaagaccgt cgctcaggat | 600 |
| tacccagaca ccaactggcg ctggcagtac tcccctgagt ccttcaccgg cactgaggtt | 660 |
| gagtacgcca aggaagttgt ggacgcagtt gttgaggtca tggatccaac tcctgagaac | 720 |
| ccaatgatca tcaacctgcc ttccaccgtt gagatgatca ccctaacgt ttacgcagac | 780 |
| tccattgaat ggatgcaccg caatctaaac cgtcgtgatt ccattatcct gtccctgcac | 840 |
| ccgcacaatg accgtggcac cggcgttggc gcagctgagc tgggctacat ggctggcgct | 900 |
| gaccgcatcg aaggctgcct gttcggcaac ggcgagcgca ccggcaacgt ctgcctggtc | 960 |
| accctggcac tgaacatgct gacccagggc gttgaccctc agctggactt caccgatata | 1020 |
| cgccagatcc gcagcaccgt tgaatactgc aaccagctgc gcgttcctga cgccacccca | 1080 |
| tacggcggcg acctggtctt caccgctttc tccggttccc accaggacgc tgtgaacaag | 1140 |
| ggtctggacg ccatggctgc caaggttcag ccaggtgcta gctccactga gtttcttgg | 1200 |
| gagcagctgc gcgacaccga atgggaggtt ccttacctgc ctatcgatcc aaaggatgtc | 1260 |
| ggtcgcgact acgaggctgt tatccgcgtg aactcccagt ccggcaaggg cggcgttgct | 1320 |
| tacatcatga agaccgatca cggtctgcag atccctcgct ccatgcaggt tgagttctcc | 1380 |
| accgttgtcc agaacgtcac cgacgctgag ggcggcgagg tcaactccaa ggcaatgtgg | 1440 |
| gatatcttcg ccaccgagta cctggagcgc accgcaccag ttgagcagat cgcgctgcgc | 1500 |
| gtcgagaacg ctcagaccga aaacgaggat gcatccatca ccgccgagct catccacaac | 1560 |
| ggcaaggacg tcaccgtcga tggccacggc aacggcccac tggctgctta cgccaacgcg | 1620 |
| ctggagaagc tgggcatcga cgttgagatc caggaataca accagcacgc ccagacctcg | 1680 | cgcgacgatg cagaagcagc cgcctacgtg ctggctgagg tcaacggccg caaggtctgg    1740 ggcgtcggca tcgctggctc catcacctac gcttcgctga aggcagtgac ctccgccgta    1800 aaccgcgcgc tggacgtcaa ccacgaggca gtcctggctg gcggcgttta a             1851

<210> SEQ ID NO 47
<211> LENGTH: 1851
<212> TYPE: DNA
<213> ORGANISM: Artificial Sequence
<220> FEATURE:
<223> OTHER INFORMATION: R558A, G561Y NT

<400> SEQUENCE: 47
atgtctccta acgatgcatt catctccgca cctgccaaga tcgaaacccc agttgggcct      60
cgcaatgaag gccagccagc atggaataag cagcgtggct cctcaatgcc agttaaccgc    120
tacatgcctt tcgaggttga ggtagaagat atttctctgc cggaccgcac ttggccagat    180
aaaaaaatca ccgttgcacc tcagtggtgt gctgttgacc tgcgtgacgg caaccaggct    240
ctgattgatc cgatgtctcc tgagcgtaag cgccgcatgt tgagctgct ggttcagatg     300 ggattcaagg aaatcgaggt cggtttccct tcagcttccc agactgattt tgatttcgtt    360
cgtgagatca tcgaaaagga catgatccct gacgatgtca ccattcaggt tctggttcag    420
gctcgtgagc acctgattcg ccgtactttt gaagcttgcg aaggcgcaaa aacgttatc     480 gtgcacttct acaactcaac ctccatcctg cagcgcaacg tggtgttccg catggacaag    540
gtgcaggtga agaagctggc taccgatgcc gctgaactga tcaagaccgt cgctcaggat    600
tacccagaca ccaactggcg ctggcagtac tcccctgagt ccttcaccgg cactgaggtt    660
gagtacgcca aggaagttgt ggacgcagtt gttgaggtca tggatccaac tcctgagaac    720
ccaatgatca tcaacctgcc ttccaccgtt gagatgatca cccctaacgt ttacgcagac    780
tccattgaat ggatgcaccg caatctaaac cgtcgtgatt ccattatcct gtccctgcac    840
ccgcacaatg accgtggcac cggcgttggc gcagctgagc tgggctacat ggctggcgct    900
gaccgcatcg aaggctgcct gttcggcaac ggcgagcgca ccggcaacgt ctgcctggtc    960
accctggcac tgaacatgct gacccagggc gttgaccctc agctggactt caccgatata   1020
cgccagatcc gcagcaccgt tgaatactgc aaccagctgc gcgttcctga gcgccaccca   1080
tacgcggccg acctggtctt caccgctttc tccggttccc accaggacgc tgtgaacaag   1140
ggtctggacg ccatggctgc caaggttcag ccaggtgcta gctccactga gtttcttgg    1200 gagcagctgc gcgacaccga atgggaggtt ccttacctgc ctatcgatcc aaaggatgtc   1260
ggtcgcgact acgaggctgt tatccgcgtg aactcccagt ccggcaaggg cggcgttgct   1320
tacatcatga agaccgatca cggtctgcag atccctcgct ccatgcaggt tgagttctcc   1380
accgttgtcc agaacgtcac cgacgctgag ggcggcgagg tcaactccaa ggcaatgtgg   1440
gatatcttcg ccaccgagta cctggagcgc accgcaccag ttgagcagat cgcgctgcgc   1500
gtcgagaacg ctcagaccga aaacgaggat gcatccatca ccgccgagct catccacaac   1560
ggcaaggacg tcaccgtcga tggccacggc aacgcccac tggctgctta cgccaacgcg    1620
ctggagaagc tgggcatcga cgttgagatc caggaataca accagcacgc cgcaacctcg   1680
tacgacgatg cagaagcagc cgcctacgtg ctggctgagg tcaacggccg caaggtctgg   1740
ggcgtcggca tcgctggctc catcacctac gcttcgctga aggcagtgac ctccgccgta   1800
aaccgcgcgc tggacgtcaa ccacgaggca gtcctggctg gcggcgttta a             1851

<210> SEQ ID NO 48
<211> LENGTH: 1851
<212> TYPE: DNA
<213> ORGANISM: Artificial Sequence
<220> FEATURE:
<223> OTHER INFORMATION: R558Q, G561D NT

<400> SEQUENCE: 48

| | | | | | |
|---|---|---|---|---|---|
| atgtctccta | acgatgcatt | catctccgca | cctgccaaga | tcgaaacccc | agttgggcct | 60 |
| cgcaatgaag | gccagccagc | atggaataag | cagcgtggct | cctcaatgcc | agttaaccgc | 120 |
| tacatgcctt | tcgaggttga | ggtagaagat | atttctctgc | cggaccgcac | ttggccagat | 180 |
| aaaaaaatca | ccgttgcacc | tcagtggtgt | gctgttgacc | tgcgtgacgg | caaccaggct | 240 |
| ctgattgatc | cgatgtctcc | tgagcgtaag | cgccgcatgt | ttgagctgct | ggttcagatg | 300 |
| ggattcaagg | aaatcgaggt | cggtttccct | tcagcttccc | agactgattt | tgatttcgtt | 360 |
| cgtgagatca | tcgaaaagga | catgatccct | gacgatgtca | ccattcaggt | tctggttcag | 420 |
| gctcgtgagc | acctgattcg | ccgtactttt | gaagcttgcg | aaggcgcaaa | aaacgttatc | 480 |
| gtgcacttct | acaactcaac | ctccatcctg | cagcgcaacg | tggtgttccg | catggacaag | 540 |
| gtgcaggtga | agaagctggc | taccgatgcc | gctgaactga | tcaagaccgt | cgctcaggat | 600 |
| tacccagaca | ccaactggcg | ctggcagtac | tcccctgagt | ccttcaccgg | cactgaggtt | 660 |
| gagtacgcca | aggaagttgt | ggacgcagtt | gttgaggtca | tggatccaac | tcctgagaac | 720 |
| ccaatgatca | tcaacctgcc | ttccaccgtt | gagatgatca | cccctaacgt | ttacgcagac | 780 |
| tccattgaat | ggatgcaccg | caatctaaac | cgtcgtgatt | ccattatcct | gtccctgcac | 840 |
| ccgcacaatg | accgtggcac | cggcgttggc | gcagctgagc | tgggctacat | ggctggcgct | 900 |
| gaccgcatcg | aaggctgcct | gttcggcaac | ggcgagcgca | ccggcaacgt | ctgcctggtc | 960 |
| accctggcac | tgaacatgct | gacccagggc | gttgaccctc | agctggactt | caccgatata | 1020 |
| cgccagatcc | gcagcaccgt | tgaatactgc | aaccagctgc | gcgttcctga | gcgccaccca | 1080 |
| tacggcggcg | acctggtctt | caccgctttc | tccggttccc | accaggacgc | tgtgaacaag | 1140 |
| ggtctgacg | ccatggctgc | caaggttcag | ccaggtgcta | gctccactga | agtttcttgg | 1200 |
| gagcagctgc | gcgacaccga | atgggaggtt | ccttacctgc | ctatcgatcc | aaaggatgtc | 1260 |
| ggtcgcgact | acgaggctgt | tatccgcgtg | aactcccagt | ccggcaaggg | cggcgttgct | 1320 |
| tacatcatga | agaccgatca | cggtctgcag | atccctcgct | ccatgcaggt | tgagttctcc | 1380 |
| accgttgtcc | agaacgtcac | cgacgctgag | ggcggcgagg | tcaactccaa | ggcaatgtgg | 1440 |
| gatatcttcg | ccaccgagta | cctggagcgc | accgcaccag | ttgagcagat | cgcgctgcgc | 1500 |
| gtcgagaacg | ctcagaccga | aaacgaggat | gcatccatca | ccgccgagct | catccacaac | 1560 |
| ggcaaggacg | tcaccgtcga | tggccacggc | aacggcccac | tggctgctta | cgccaacgcg | 1620 |
| ctggagaagc | tgggcatcga | cgttgagatc | caggaataca | accagcacgc | ccagacctcg | 1680 |
| gatgacgatg | cagaagcagc | cgcctacgtg | ctggctgagg | tcaacggccg | caaggtctgg | 1740 |
| ggcgtcggca | tcgctggctc | catcacctac | gcttcgctga | aggcagtgac | ctccgccgta | 1800 |
| aaccgcgcgc | tggacgtcaa | ccacgaggca | gtcctggctg | gcggcgttta | a | 1851 |

<210> SEQ ID NO 49
<211> LENGTH: 1851
<212> TYPE: DNA
<213> ORGANISM: Artificial Sequence
<220> FEATURE:
<223> OTHER INFORMATION: R558Q, G561R NT

<400> SEQUENCE: 49

```
atgtctccta acgatgcatt catctccgca cctgccaaga tcgaaacccc agttgggcct      60
cgcaatgaag gccagccagc atggaataag cagcgtggct cctcaatgcc agttaaccgc     120
tacatgcctt tcgaggttga ggtagaagat atttctctgc cggaccgcac ttggccagat     180
aaaaaaatca ccgttgcacc tcagtggtgt gctgttgacc tgcgtgacgg caaccaggct     240
ctgattgatc cgatgtctcc tgagcgtaag cgccgcatgt ttgagctgct ggttcagatg     300
ggattcaagg aaatcgaggt cggtttccct tcagcttccc agactgattt tgatttcgtt     360
cgtgagatca tcgaaaagga catgatccct gacgatgtca ccattcaggt tctggttcag     420
gctcgtgagc acctgattcg ccgtactttt gaagcttgcg aaggcgcaaa aaacgttatc     480
gtgcacttct acaactcaac ctccatcctg cagcgcaacg tggtgttccg catggacaag     540
gtgcaggtga agaagctggc taccgatgcc gctgaactga tcaagaccgt cgctcaggat     600
tacccagaca ccaactggcg ctggcagtac tcccctgagt ccttcaccgg cactgaggtt     660
gagtacgcca aggaagttgt ggacgcagtt gttgaggtca tggatccaac tcctgagaac     720
ccaatgatca tcaacctgcc ttccaccgtt gagatgatca cccctaacgt ttacgcagac     780
tccattgaat ggatgcaccg caatctaaac cgtcgtgatt ccattatcct gtccctgcac     840
ccgcacaatg accgtggcac cggcgttggc gcagctgagc tgggctacat ggctggcgct     900
gaccgcatcg aaggctgcct gttcggcaac ggcgagcgca ccggcaacgt ctgcctggtc     960
accctggcac tgaacatgct gacccagggc gttgaccctc agctggactt caccgatata    1020
cgccagatcc gcagcaccgt tgaatactgc aaccagctgc gcgttcctga gcgccaccca    1080
tacggcggcg acctggtctt caccgctttc tccggttccc accaggacgc tgtgaacaag    1140
ggtctggacg ccatggctgc caaggttcag ccaggtgcta gctccactga gtttcttgg     1200
gagcagctgc gcgacaccga atgggaggtt ccttacctgc ctatcgatcc aaaggatgtc    1260
ggtcgcgact acgaggctgt tatccgcgtg aactcccagt ccggcaaggg cggcgttgct    1320
tacatcatga agaccgatca cggtctgcag atccctcgct ccatgcaggt tgagttctcc    1380
accgttgtcc agaacgtcac cgacgctgag ggcggcgagg tcaactccaa ggcaatgtgg    1440
gatatcttcg ccaccgagta cctggagcgc accgcaccag ttgagcagat cgcgctgcgc    1500
gtcgagaacg ctcagaccga aaacgaggat gcatccatca ccgccgagct catccacaac    1560
ggcaaggacg tcaccgtcga tggccacggc aacggcccac tggctgctta cgccaacgcg    1620
ctggagaagc tgggcatcga cgttgagatc caggaataca accagcacgc ccagacctcg    1680
cgcgacgatg cagaagcagc cgcctacgtg ctggctgagg tcaacggccg caaggtctgg    1740
ggcgtcggca tcgctggctc catcacctac gcttcgctga aggcagtgac ctccgccgta    1800
aaccgcgcgc tggacgtcaa ccacgaggca gtcctggctg gcggcgttta a             1851
```

<210> SEQ ID NO 50
<211> LENGTH: 1851
<212> TYPE: DNA
<213> ORGANISM: Artificial Sequence
<220> FEATURE:
<223> OTHER INFORMATION: R558Q, G561Y NT

<400> SEQUENCE: 50

```
atgtctccta acgatgcatt catctccgca cctgccaaga tcgaaacccc agttgggcct      60
cgcaatgaag gccagccagc atggaataag cagcgtggct cctcaatgcc agttaaccgc     120
tacatgcctt tcgaggttga ggtagaagat atttctctgc cggaccgcac ttggccagat     180
```

```
aaaaaaatca ccgttgcacc tcagtggtgt gctgttgacc tgcgtgacgg caaccaggct    240
ctgattgatc cgatgtctcc tgagcgtaag cgccgcatgt ttgagctgct ggttcagatg    300
ggattcaagg aaatcgaggt cggtttccct tcagcttccc agactgattt tgatttcgtt    360
cgtgagatca tcgaaaagga catgatccct gacgatgtca ccattcaggt tctggttcag    420
gctcgtgagc acctgattcg ccgtactttt gaagcttgcg aaggcgcaaa aaacgttatc    480
gtgcacttct acaactcaac ctccatcctg cagcgcaacg tggtgttccg catggacaag    540
gtgcaggtga agaagctggc taccgatgcc gctgaactga tcaagaccgt cgctcaggat    600
tacccagaca ccaactggcg ctggcagtac tcccctgagt ccttcaccgg cactgaggtt    660
gagtacgcca aggaagttgt ggacgcagtt gttgaggtca tggatccaac tcctgagaac    720
ccaatgatca tcaacctgcc ttccaccgtt gagatgatca ccctaacgt ttacgcagac    780 tccattgaat ggatgcaccg caatctaaac cgtcgtgatt ccattatcct gtccctgcac    840
ccgcacaatg accgtggcac cggcgttggc gcagctgagc tgggctacat ggctggcgct    900
gaccgcatcg aaggctgcct gttcggcaac ggcgagcgca ccggcaacgt ctgcctggtc    960
accctggcac tgaacatgct gacccagggc gttgaccctc agctggactt caccgatata   1020
cgccagatcc gcagcaccgt tgaatactgc aaccagctgc gcgttcctga gcgccaccca   1080 tacgcggcg acctggtctt caccgctttc tccggttccc accaggacgc tgtgaacaag   1140
ggtctggacg ccatggctgc caaggttcag ccaggtgcta gctccactga agtttcttgg   1200
gagcagctgc gcgacaccga atgggaggtt ccttacctgc ctatcgatcc aaaggatgtc   1260
ggtcgcgact acgaggctgt tatccgcgtg aactcccagt ccggcaaggg cggcgttgct   1320
tacatcatga agaccgatca cggtctgcag atccctcgct ccatgcaggt tgagttctcc   1380
accgttgtcc agaacgtcac cgacgctgag ggcggcgagg tcaactccaa ggcaatgtgg   1440
gatatcttcg ccaccgagta cctggagcgc accgcaccag ttgagcagat cgcgctgcgc   1500
gtcgagaacg ctcagaccga aaacgaggat gcatccatca ccgccgagct catccacaac   1560
ggcaaggacg tcaccgtcga tggccacggc aacggcccac tggctgctta cgccaacgcg   1620
ctggagaagc tgggcatcga cgttgagatc caggaataca accagcacgc ccagacctcg   1680
tacgacgatg cagaagcagc cgcctacgtg ctggctgagg tcaacggccg caaggtctgg   1740
ggcgtcggca tcgctggctc catcacctac gcttcgctga aggcagtgac ctccgccgta   1800
aaccgcgcgc tggacgtcaa ccacgaggca gtcctggctg gcggcgttta a            1851
```